A US005856331A

United States Patent [19]
Bursten et al.

[11] Patent Number: 5,856,331
[45] Date of Patent: Jan. 5, 1999

[54] METHOD FOR PREVENTING TISSUE INJURY FROM HYPOXIA

[75] Inventors: Stuart L. Bursten, Snoqualmie; Jack W. Singer; Glenn C. Rice, both of Seattle, all of Wash.

[73] Assignee: Cell Therapeutics, Inc., Seattle, Wash.

[21] Appl. No.: 948,747

[22] Filed: Oct. 10, 1997

Related U.S. Application Data

[63] Continuation of Ser. No. 353,756, Dec. 12, 1994, which is a continuation-in-part of Ser. No. 152,117, Nov. 12, 1993, abandoned.

[51] Int. Cl.[6] .................. A61K 31/415; A61K 31/42; A61K 31/425; A61K 31/52
[52] U.S. Cl. .................. 514/263; 514/183; 514/222.5; 514/223.5; 514/224.2; 514/226.8; 514/227.5; 514/228.8; 514/229.2; 514/230.5; 514/230.8; 514/237.8; 514/241; 514/242; 514/243; 514/246; 514/247; 514/248; 514/249; 514/255; 514/256; 514/258; 514/259; 514/261; 514/262; 514/263; 514/270; 514/274
[58] Field of Search .................. 514/263, 255; 544/272

[56] References Cited

U.S. PATENT DOCUMENTS

| 4,515,795 | 5/1985 | Hinze et al. | 514/263 |
|---|---|---|---|
| 5,272,153 | 12/1993 | Mandell et al. | 514/263 |
| 5,409,935 | 4/1995 | Schubert et al. | 514/265 |
| 5,641,783 | 6/1997 | Klein et al. | 514/263 |

FOREIGN PATENT DOCUMENTS

| 0 462 506 A1 | 12/1991 | European Pat. Off. . |
|---|---|---|
| 2 207 860 | 8/1973 | Germany . |
| WO 92/07585 | 5/1992 | WIPO . |
| WO 92/21344 | 12/1992 | WIPO . |
| WO 93/17684 | 9/1993 | WIPO . |

OTHER PUBLICATIONS

Abraham, E. et al., "Hemorrhage in Mice Produces Alterations in B Cell Repertoires", *Cellular Immunology*, 122, pp. 208–217 (1989).
Abraham, E. et al., "Effects of Hemorrhage on Interleukin–1 Production", *Circulatory Shock*, 25:33–40 (1988).
Abraham, E. et al., "Hemorrhage Produces Abnormalities in Lymphocyte Function and Lymphokine Generation", *The Journal of Immunology*, vol. 142, 899–906, No. 3 (1989).
Baker, C. C. et al., "Epidemiology of Trauma Deaths", *The American Journal of Surgery*, pp. 144–150 (1980).
Bursten, S. et al., "CT–150 1R Inhibits Rapid Synthesis of Specific Phosphatidic Acid (PA) Species Following Stimulation of Tumor Necrosis Factor Alpha (TNFα) Type I but not Type II Receptors" (Abstract), *Hematopoietic Growth Factors–II*, p. 1436. (1990).

Ertel, W. et al., "Anti–TNF Monoclonal Antibodies Prevent Haemorrhage–Induced Suppression of Kupffer Cell Antigen Presentation and MHC Class II Antigen Expression," *Immunology*, 74 pp. 290–297 (1991).
Hammerschmidt, D. et al., "Association of Complement Activation and Elevated Plasma–C5a with Adult Respiratory Distress Syndrome", *The Lancet*, pp. 947–845, May 3, 1980.
Hoch, R. C. et al., "Effects of Accidental Trauma on Cytokine and Endotoxin Production," *Critical Care Medicine*, 21, No. 6, (1993).
Klöcking, H.–P. et al., "Release of Plasminogen Activator By Pentoxifyline and its Major Metabolite", *Thrombosis Research* 46; pp. 747–750 (1987).
Leff, Jonathan et al., "Serum Antioxidants as Predictors of Adult Respiratory Distress Syndrome in Patients with Sepsis," *The Lancet*, 341, pp. 777–780, (1993).
Marzi, Ingo, "Value of Superoxide Dismutase for Prevention of Multiple Organ Failure After Multiple Trauma", *The Journal of Trauma*, 35, No. 1, pp. 110–120. (1991).
McElvaney, N. et al., "Aerosol α1–antitrypsin Treatment for Cystic Fibrosis", *The Lancet*, 337, pp. 392–394, (1991).
Meldrum, Daniel R. et al., "Diltiazem Restores IL–2, IL–3, IL–6, and IFN–γ Synthesis and Decreases Host Susceptibility to Sepsis following Hemorrhage", *Journal of Surgical Research*, 51, pp. 158–164 (1991).
Moore, F. A. et al., "Gut Bacterial Translocation via the Portal Vein: A Clinical Perspective with Major Torso Trauma", *The Journal of Trauma*, 31, No. 5, pp. 629–638 (1991).
Nakamura, H. et al., "Neutrophil Elastase in Respiratory Epithelial Lining Fluid of Individuals with Cystic Fibrosis Induces Interleukin–8 Gene Expression in a Human Bronchial Epithelial Cell Line", *The Journal of Clinical Investigation, Inc.*, 89, pp. 1478–1484 (1992).
Pepe, Paul et al., "Clinical Predictors of the Adult Respiratory Distress Syndrome", *The American Journal of Surgery*, pp. 124–130. (1992).
Repine, John E., "Scientific Perspective on Adult Respiratory Distress", *The Lancet*, 339, (1992).
Rice, G. et al., "Protection Against Endotoxic Shock in Mice by a New Class of Synthetic Phospholipid Second Messenger Inhibitors", *Cytokines and Cytokine Receptors: From Cloning to the Clinic* (Abstract), p. 107. (1991).
Rice, Glenn et al., "Protection from Endotoxic Shock in Mice by Pharmacologic Inhibition of Phosphatidic Acid", *Proc. Natl. Acad. Sci. USA*, 91, pp. 3857–3861 (1994).

(List continued on next page.)

*Primary Examiner*—Theodore J. Criares
*Attorney, Agent, or Firm*—Foley & Lardner

[57] ABSTRACT

There is disclosed a method for preventing tissue injury caused by tissue hypoxia and reoxygenation, comprising administering a compound that inhibits signal transduction by inhibiting cellular accumulation of linoleoyl phosphatidic acid (PA) through an inhibition of the enzyme LPAAT (lysophosphatidic acyltransferase).

7 Claims, 9 Drawing Sheets

OTHER PUBLICATIONS

Rinehart, John et al., "Corticosteroid Modulation of Interleukin–1 Hematopoietic Effects and Toxicity in a Murine System", *Blood*, 84, No. 5 (pp. 1457–1463 (1994).

Riordan, John et al., "Identification of the Cystic Fibrosis Gene: Cloning and Characterization of Complementary DNA" *Science*, 245, pp. 1066–1073, (1989).

Robinson, A. et al., "Effects of Haemorrhage on Bacterial Antigen Specific Pulmonary Plasma Cell Function", *Clin. Exp. Immunol.*, 88, pp. 124–128 (1992).

Robinson, A. and Abraham, E., "Hemorrhage in Mice Produces Alterations in Pulmonary B Cell Repertoires", *The Journal of Immunology*, 146; pp. 3734–3739 (1990).

Semmler, J. et al., "Xanthine Derivatives: Comparison between Suppression of Tumour Necrosis Factor–α Production and Inhibition of cAMP Phosphodiesterase Activity", *Immunology*, 78, pp. 52 525, (1993).

Shenkar, R. and Abraham E., "Effects of Hemorrhage on Cytokine Gene Transcription", *Lymphokine and Cytokine Research*, 12, No. 4, pp. 237–246 (1993).

Sibille, Y. and Reynolds, H. "Macrophages and Polymorphonuclear Neutrophils in Lung Defense and Injury", *Am. Rev. Respir. Dis.*, 141, pp. 471–501 (1990).

Sullivan, Gail et al., "Inhibition of the Inflammatory Action of Interleukin–1 and Tumor Necrosis Factor (Alpha) on Neutrophil Function by Pentoxifyline" *Infection and Immunity*, 56, pp. 1722–1729 (1988).

Terada, L. et al., "Hypoxia Injures Endothelial Cells by Increasing Endogenous Xanthine Oxidase Activity", *Proc. Natl. Acad. Sci. USA*, 89, pp. 3362–3366 (1992).

Tranquille, N. and Emeis, J. J., "The Effect of Pentoxifylline (Trental) and Two Analogues, BL 194 and HWA 448, on the Release of Plasminogen Activators and von Willebrand Factor in Rats", *Journal of Cardiovascular Pharmacology*, 18, pp. 35–42 (1991).

Chemical Abstracts; vol. 119; No. 224878r (Harada et al.) 1989.

METHOD FOR PREVENTING TISSUE INJURY FROM HYPOXIA

CROSS REFERENCE TO RELATED APPLICATION

This application is a continuation, of application Ser. No. 08/353,756, filed Dec. 12, 1994, pending which is a Continuation-in-Part of application Ser. No. 08/152,117, filed Nov. 12, 1993, now abandoned.

TECHNICAL FIELD OF THE INVENTION

The present invention provides a method for preventing tissue injury caused by tissue hypoxia, comprising administering a compound that inhibits signal transduction by inhibiting cellular accumulation of a linoleate-containing phosphatidic acid (PA) through an inhibition of the enzyme LPAAT (lysophosphatidic acyltransferase).

BACKGROUND OF THE INVENTION

Acute lung injury, manifested clinically as the Adult Respiratory Distress Syndrome (ARDS) occurs in more than 50% of patients following severe injury and blood loss. ARDS is characterized clinically by decreasing lung compliance and severe impairment of oxygen diffusion (Hammerschmidt et al., *Lancet* 1:947, 1980; Moore et al., *J. Trauma* 31:629, 1991; Pepe et al., *Am. J. Surg.* 144:124, 1982; and Baker et al., *Am. J. Surg.* 140:144, 1980). Histologic changes in the lungs which are present in this setting include neutrophil and mononuclear infiltrates, interstitial edema, intraaveolar hemorrhage, and fibrin formation. In injured patients, increased plasma levels of proinflammatory cytokines, such as IL-6 and IL-8, as well as evidence of endothelial activation, as shown by elevated circulating titers of soluble intracellular adhesion molecules (sICAM), are found within one hour of blood loss and trauma Bronchoalveolar lavages obtained from patients with ARDS contain elevated titers of IL-1β and TNFα. Also, release of proinflammatory cytokines, such as IL-1 and TNFα is increased after blood loss (Abraham et al., *Circ. Shock* 25:33, 1988; Meldrum et al., *J. Surg. Res.* 51:158, 1991; and Ertel et al., *Immunology* 74:290, 1991). Studies examining the 4 hour period. immediately following hemorrhage demonstrated increased levels of mRNA for proinflammatory cytokines, including IL-1α, IL-1β, TNFα, IL-6 and IFN-γ, among cells isolated from mucosal sites (e.g., lungs and intestines) but not among splenocytes or peripheral blood mononuclear cells (Shenkar and Abraham, *Lymphokine Cytokine Res.* 12:237, 1993). It has been postulated that increased local production of proinflammatory cytokines may contribute to lung injury in this setting. Blood loss is a central factor in the pathophysiologic instability that follows trauma, and has been associated with alterations in macrophage, T cell and B cell function. Hemorrhage does not result in changes in absolute or relative numbers of T cell or B cell subsets in the spleen, lymph nodes, blood or lung (Abraham and Freitas, *J. Immunol.* 142:899, 1989; Robinson and Abraham, *J. Immunol.* 145:3734, 1990; Abraham et al. *Cell. Immunol.* 122:208, 1989; and Robinson et al., *Clin. Exp. Immunol.* 88:124, 1992).

It is possible that the local ischemia and/or hypoxia created by redistribution of blood flow in visceral (splanchnic) organs such as the gut (particularly the small intestine) and kidney are responsible for induction of the cytokine cascades, which in turn, result in distal organ injury. Evidence exists demonstrating that absolute and relative blood flow levels within these organs fall within minutes of volume shifts, hemorrhage, or induction of other causes of shock (textbook Hypertension). There is, therefore, a need in the art for compounds which (1) prevent initial production of proinflammatory cytokine mediators in response to decreased perfusion and (2) prevent redistribution of microcirculation induced by these proinflammatory cytokine mediators.

In severely injured patients, serum levels of IL-6 and IL-8 are increased within one hour or injury, but do not appear to predict which patients will develop ARDS (Hoch et al., *Crit. Care Med.* 21:839, 1993). No detectable IL-1α, IL-1β. or endotoxin was found in patient samples obtained over 5 days post-injury in these patients (Hoch et al., infra.). Moreover, plasma levels of TNF are rarely increased following severe injury and there does not appear to be any correlation between the presence or amount of TNFα and the development of ARDS or organ system dysfunction.

Based upon experiments ongoing which examine the biochemical events following severe injury with blood loss and resulting tissue hypoxia, even if treated medicinally with fluids and/or blood products still results in inflammatory changes in the lungs and other organs.

Neutrophils are important for host-defense against bacterial and other infections. This is suggested as a consequence of observations that there is an increased infections seen in patients with insufficient numbers of neutrophils or with neutrophils with genetically determined abnormalities (e.g., chronic granulomatous disease). Antibiotics are available to treat infections (ie., be directly cytotoxic to the infectious agent), but there are no specific therapies available to treat septic shock or the compounding organ dysfunction that follows from septic shock or other causes of tissue hypoxia/ischemia. Therefore it may be necessary to risk decreasing neutrophil function (as direct cytotoxic agents against the pathogen) to prevent fatal lung injury and other organ dysfunction.

Cystic fibrosis (CF) is a lethal hereditary disorder caused by mutations of the cystic fibrosis transmembrane conductance regulator (CFTR) gene. The CFTR gene product is a 168 kD glycosylated membrane protein that functions as a chloride channel regulated by cytoplasmic protein kinases (Riordan et al., *Science* 245:1066, 1989). Although the link between mutations in the CFTR gene and the pathogenesis of CF are not understood, the lethal clinical manifestations of CF are related to a thick, infected mucus and chronic neutrophil-dominated inflammation of the epithelial surface of the airways. A large number of neutrophils place the airway epithelium in jeopardy consequent to exposure to potent neutrophil mediators, including neutrophil elastase (NE), and reactive oxygen species, and a variety of cytokines (Sibille and Reynolds, *Am. Rev. Respir. Dis.* 141:471, 1990; and McElvaney et al., *Lancet 337:392, 1991*). Although critical to host defense, neutrophils cause progressive damage to airway epithelium by virtue of their potent mediators, most significantly NE. Not only can NE damage epithelial cells by direct proteolytic effects, but it can also hinder host defense by interfering with ciliary clearance, increasing mucus production, cleaving immunoglobulin and complement, and by impairing phagocytosis and killing of *Pseudomonas aeruginosa* by neutrophils. The fluid lining the respiratory epithelium in CF contains large numbers of activated neutrophils and active NE, and the NE in CF is capable of inducing bronchial epithelium cells to express the gene for IL-8 and release neutrophil chemotactic activity as properties of IL-8 (Nakamura et al., *J. Clin. Invest.* 89:1478, 1992). Neutrophils in the thick mucus are rendered hypoxic. Therefore there is a need in the art to find a therapeutic compound capable of inhibiting IL-8 signaling and thereby provide treatment for CF.

Hypoxic injury generates oxidative injury. For example, serum antioxidants may be predictors of ARDS in sepsis patients. At an initial diagnosis of sepsis (6–24 hr before development of ARDS), serum manganese superoxide dismutase concentration and catalase activity were higher is a study of patients (6) who subsequently developed ARDS as compared to patients (20) who did not develop ARDS (Leff et al., *Lancet* 341:777, 1993). Accelerated intravascular generation of oxygen radicals from stimulated neutrophils, circulating xanthine oxidase, and other sources have been implicated in the pathogenesis of sepsis and ARDS (Repine, *Lancet* 339:466, 1992). Moreover, in vitro, exposure to decreasing oxygen tensions progressively increased xanthine dehydrogenase (XD) and xanthine oxidase (XO) activities over 48 hr in cultured pulmonary artery endothelial cells without altering XD/XO ratios. Oxygen tension negatively modulates XO and its precursor XD, and was associated with an increase in release of $O_2^-$ (Terada et al., *Proc. Natl. Acad. Sci. USA* 89:3362, 1992). This connection to hypoxia and multiple organ failure or dysfunction is further strengthened by a clinical trial report that recombinant human superoxide dismutase administered in a placebo-controlled trial attenuated multiple organ failure, shortened intensive care therapy, and decreased the release of inflammatory mediators (Marzl et al., *J. Trauma* 35:110, 1993).

SUMMARY OF THE INVENTION

The present invention provides a method for inhibiting hypoxic injury (comprising hypoxia and reoxygenation) to tissues and organ dysfunction, comprising administering a compound that inhibits signal transduction through cellular accumulation of linoleate-containing phosphatidic acid (linoleoyl-PA). Preferably, the compound is an organic molecule that inhibits generation of linoleoyl-PA that exerts its activity through inhibition of lysophosphatidic acyltransferase (LPAAT). Hypoxic injury is manifest as: (1) multiorgan dysfunction following shock caused by hemorrhage, severe cardiac dysfunction, severe burns, or sepsis, (2) CNS tissue injury following occlusive cerebrovascular accidents (stroke), (3) cardiovascular tissue injury following myocardial infarction, (4) organ dysfunction following transplantation of kidney, liver, heart, lung, or bowel, (5) organ damage following vascular surgery in any site, such as coronary artery, cerebral vasculature, or peripheral angioplasty, (6) high altitude pulmonary edema (altitude sickness), (7) acidosis, such as diabetic acidosis, drug-induced acidosis (e.g., salicylate poisoning), and renal acidosis, (8) prevention of organ transplant rejection due to hypoxia, or (10) hypoxia-mediated neurodegenerative diseases, such as Parkinsons disease, Huntington's disease, Alzheimer's disease and ALS (Amyotrophic Lateral Sclerosis). Hypoxic injury to neutrophils is also a component of cystic fibrosis, therefore, the present method includes treatment (to prevent further progression) of cystic fibrosis, comprising administering an effective amount of a compound that can effectively inhibit LPAAT activation in response to a hypoxia and reoxygenation.

DETAILED DESCRIPTION OF THE INVENTION

Figure 1:
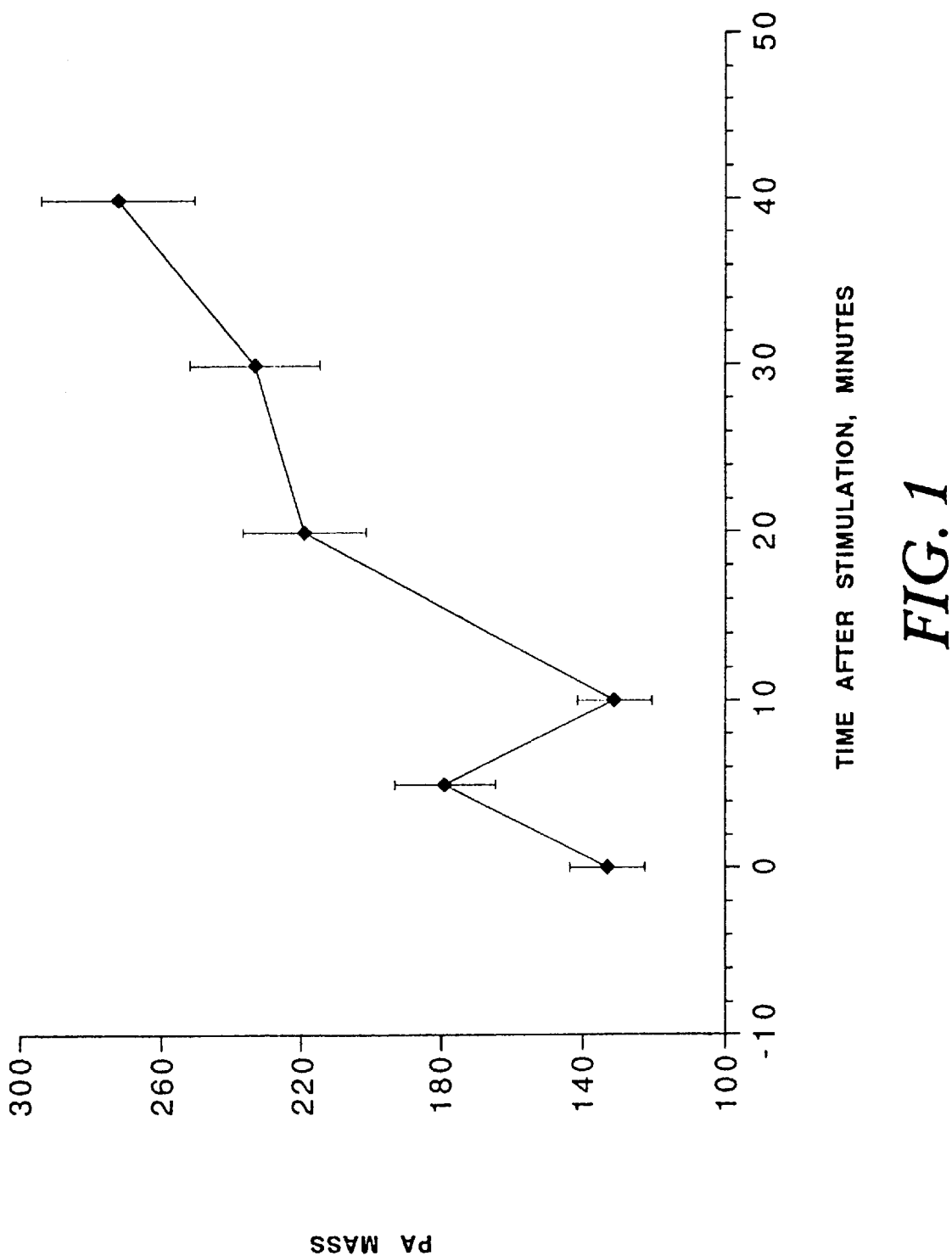
FIG. 1 shows the effect of hypoxia on PA concentrations in polymorphonuclear leukocytes (PMNs) by measuring PA mass after inducing hypoxia for 1 hour and reoxygenating for the times shown on the X axis. Cell PA concentrations rise over time in response to reoxygenation after hypoxia.

The inciting event in a number the clinical conditions associated with decreased tissue perfusion (ischemia) is tissue hypoxia. When hypoxic tissue is reoxygenated by improved perfusion (reperfusion), the cells begin to manufacture large amounts of linoleoyl-PA through activation of LPAAT. The linoleoyl-PA in turn may activate other important phospholipid controlling enzymes such as $PLA_2$ (phospholipase $A_2$) and lyso phospholipase D producing the other active molecule, lyso PA. These phospholipids directly activate transcription of proinflammatory cytokines such as TNFα, IFN-γ and IL-1 which in turn activate secondary inflammatory mediators including IL-8, IL-6, and platelet activating factor. These reactive cytokines mediate distant tissue effects such as multiorgan dysfunction, that occur after hypoxic injury. In addition to stimulating the production of cytokines, PA side chains are converted to (9- and 13-hydroxyoctadecadienoic acids) HODE which also act as circulating mediators of inflammation. Through prevention of the activation of LPAAT in hypoxic cells, compounds, such as the genus of compounds described herein, prevent distant and local toxic effects associated with hypoxia and reperfusion.

Hemorrhage (from any cause) leads to generalized decreased tissue oxygenation through decreased perfusion. Following reperfusion that comes after repletion of the blood volume, a systemic inflammatory response develops, leading to lung injury. A prototypic LPAAT inhibitor, Lisofylline, completely prevented lung injury in a rodent model described herein, along with suppressing proinflammatory cytokines associated with tissue response to hypoxiareperfusion.

Proinflammatory cytokines, such as IL-8, IL-1β and TNFα, can be increased through activation of lipid intracellular signaling pathways resulting in increases in intracellular levels of species specific phosphatidic acid (PA) and diacylglycerol (DAG). Various subtypes of DAG stimulate several secondary signaling processes, such as activation of protein kinase C and acidic sphingomyelinase. Besides functioning as lipid second messenger intermediates, PA species and PA precursors enhance $CA^{+2}$ flux, phospholipase C activity, are mitogenic for certain cell types, and inhibit GAP-ras interactions.

PA is produced by membrane associated lysophosphatidic acyltransferase (LPAAT) and is converted to DAG via phosphatidate phosphohydrolase (PAH). The drug pentoxifylline (1-(5-oxohexyl)3,7-dimethylxanthine) is an extremely weak inhibitor of LPAAT activity, requiring concentrations of drug well in excess of those concentrations that could be clinically achievable (e.g., >1 mM). However, Lisofylline is about 800 to 1000 fold more potent than pentoxifylline in inhibiting PA and DAG generation. Therefore, pentoxifylline is not a functional LPAAT inhibitor.

Without being bound by theory, however, it appears that hypoxia results in immediate membrane perturbations, leading in turn to activation of a complex of phospholipid signal regulatory enzymes formed into a complex that includes LPAAT within the complex and an initiation of membrane remodeling. Further, ischemia or reperfusion results in metabolism of added linoleate-containing PA as follows: (1) conversion of sn-2-linoleoyl PA to linoleoyl DAG by phosphatidate phosphohydrolase, (2) followed by DG lipase release of linoleate and ACAT (acyl CoA: cholesterol acyl transferase) conversion of linoleate + cholesterol to cholesteryl linoleate. This linoleate becomes the precursor of both HODEs. Thus, membrane perturbation results in: (1) formation of a linoleate-containing PA, which activates the cells and supports membrane activation by changing the nature of the membrane to a more fluid conformation (which also supports vesicle fusion and increased pino- and exocytosis), (2) production of a distal and intercellularly operating inflammatory mediators, 9- and 13-HODE, which are highly phlogistic and/or toxic, and (3) PA is in and of itself a stimulant of alkyl-PA by way of phospholipase D. Therefore, a positive feedback loop is created by this mechanism. In addition, peroxides and peroxidated fatty acids are direct stimulants of PLD (Natarajan et al., *J. Biol. Chem.* 268:930, 1993) which, in turn, causes enhanced production of PA, and creates a parallel stimulatory positive feedback loop.

The synthesis of linoleoyl-PAs and HODEs is supported by superoxide/peroxide formation that is also associated with reperfusion/ischemia. These compounds (HODEs, linoleate-containing) PA, and lyso-PA (also produced by the pathway)) are, in themselves, vasoactive compounds which lead to shifts in tissue microcirculation and, hence, perfusion. Therefore, the intense production of PA and associated lyso-PA's, followed by HODEs, in hypoxic neutrophils indicates that a phospholipid signaling pathway, having linoleate-containing PA as an intermediate ("the Pathway"), is activated under conditions of hypoxia/ischemia and leads to the usual dire consequences.

Lisofylline is a direct inactivator and competitive inhibitor of LPAAT activated by IL-1. Therefore, the action of Lisofylline, as a representative LPAAT and IL-1 inhibitor, is two-fold in preventing egress of neutrophils into ischemic areas, and then preventing production of mediators that exacerbate or directly mediate hypoxic injury to cells.

Therefore: (1) hypoxia causes membrane perturbations, due to changes in double bond insertion, or with peroxidation on reperfusion; (2) the LPAAT complex is activated, generating linoleoyl PA from fatty acids and PE; (3) peroxidation products and linoleoyl PA together generate alkyl PA from PE through activation of PLD; this creates a positive feedback loop of some potency which an LPAAT inhibitor (such as Lisofyline as a prototype LPAAT inhibitor) shuts down; (4) formation of linoleoyl PA is associated with increased synthesis of HODEs, further driving the PA pathways; (5) HODE, PA, and lyso-PA are vasoactive and may exacerbate microcirculation redistribution and thus enhance ischemia/hypoxia; (6) an LPAAT inhibitor, by preventing initiation of linoleate transition from free fatty acid/PC/PE to PA and HODE, also blocks this cycle. Taken together, these data show that compounds that cause an LPAAT inhibition are effective for treating or preventing diseases caused by hypoxia/ischenia.

Therefore, the important initiating event for hypoxic/ischemic tissue injury, that later is manifest as one of the listed indications, is membrane perturbation. Membrane perturbation is an initial unifying event in underperfusion (i.e., hypoxia) and ischemia. Reperfusion merely exacerbates the situation by producing lipid peroxidation intermediates. Thus; any of the foregoing indications can be effectively treated or prevented by an effective amount of Lisofylline or another LPAAT inhibitor through inhibition of LPAAT activation and the consequent inhibition of linoleoyl PA and HODE formation. It is apparent that ARSS (a model hypoxia-induced indication) and tissue ischemic damage in general may be largely dependent on final pathway generation of linoleoyl PA and HODE.

A murine hemorrhage and resuscitation model was developed to duplicate a clinical setting post-injury where hemorrhage is followed by restoration of blood volume through transfusion. Blood loss, even if resuscitated or replaced within one hour, was associated with histologic changes in the lungs consistent with acute lung injury and ARDS. In particular, the lungs of mice subjected to removal of 30% blood volume with return of the shed blood one hour later showed neutrophil and mononuclear infiltrates, intraaveolar hemorrhage, and interstitial edema when examined 3 days following hemorrhage. In addition, increased expression of mRNA for proinflammatory cytokines was present among intraparachymal pulmonary mononuclear cells and alveolar macrophages as soon as one hour after hemorrhage and continued to be apparent over a three day post-hemorrhage period preceding development of acute lung injury. In particular, levels of mRNA for IL-1$\beta$, IL-6, TNF$\alpha$ and IFN-$\gamma$ were all consistently found to be increased within the lungs over the 3 day post-hemorrhage period. Therefore, enhancement of proinflammatory cytokine gene transcription is an important mechanism contributing to frequent development of acute lung injury following severe blood loss due to injury and other diseases mediated by tissue hypoxia.

Lisofylline is an inhibitor of LPAAT and prevents intracellular generation of a nonlinoleoyl PA species in response to a proinflammatory stimulus, in part, by blocking signaling through the Type I IL-1 receptor and also blocking IL-8 signaling. This compound was investigated as a prototype for all LPAAT inhibitors that manifest a significant diminution in the intracellular rise of linoleoyl PA. Lisofylline was investigated for its effects on biochemical and histologic markers of pulmonary inflammation following hemorrhage and resuscitation. Lisofylline exhibited potent actions in diminishing increases in proinflammatory cytokine expression as well as histopathologic findings of acute lung injury when administered after severe blood loss. A murine hemorrhage and resuscitation model was conducted to duplicate a clinical setting post-injury where hemorrhage is followed by restoration of blood volume through transfusion. Blood loss, even if resuscitated within one hour, was associated with histologic changes in the lungs consistent with acute lung injury and ARDS. In particular, the lungs of mice subjected to removal of 30% blood volume with return of the shed blood one hour later showed neutrophil and mononuclear infiltrates, intraaveolar hemorrhage, and interstitial edema when examined 3 days following hemorrhage. In addition, increased expression of mRNA for proinflammatory cytokines was present along with intraparenchymal pulmonary mononuclear cells and alveolar macrophages as soon as one hour after hemorrhage and continued to be apparent over a 3 day post-hemorrhage period producing the development of acute lung injury. In particular, levels of mRNA for IL-1β, IL-6, TNFα, and IFN-γ all were consistently found to be increased within the lungs over the 3 day post-hemorrhage period, suggesting that enhancement of proinflammatory cytokine gene transcription is an important mechanism contributing to the frequent development of acute lung injury following severe blood loss and injury. Because of the ability of Lisofylline to block proinflammatory cytokine generation as well as cytokine induced intracellular lipid second messenger signaling and activation, the effects of this agent on biochemical and histologic markers of pulmonary inflammation following hemorrhage and resuscitation was examined. The present experiments demonstrate that Lisofylline (a prototype LPAAT inhibitor) has potent actions in diminishing the increases in proinflammatory pulmonary cytokine expression as well as the histopathologic findings of acute lung injury when administered after severe blood loss.

The data obtained for Lisofylline, and described in the examples herein, shows that LPAAT inhibitor compounds whose mechanism of action causes an inhibition of linoleoyl-PA in response to a proinflammatory stimulus are useful for treating or preventing diseases mediated by hypoxic (and subsequent reoxygenation) tissue injury. Such diseases include: (1) multiorgan dysfunction following shock caused by hemorrhage, severe cardiac dysfunction, severe burns, or sepsis, (2) CNS tissue injury following occlusive cerebrovascular accidents (stroke), (3) cardiovascular tissue injury following myocardial infarction, (4) organ dysfunction following transplantation of kidney, liver, heart, lung, or bowel, (5) organ damage following vascular surgery in any site, such as coronary artery, cerebral vasculature, or peripheral angioplasty, (6) high altitude pulmonary edema (altitude sickness), (7) acidosis, such as diabetic acidosis, drug-induced acidosis (e.g., salicylate poisoning), and renal acidosis, (8) prevention of organ transplant rejection due to hypoxia, or (10) hypoxia-mediated neurodegenerative diseases, such as Parkinsons disease, Huntington's disease, Alzheimer's disease and ALS (Amyotrophic Lateral Sclerosis). Hypoxic injury to neutrophils is also a component of cystic fibrosis, therefore, the present method includes treatment (to prevent further progression) of cystic fibrosis, comprising administering an effective amount of a compound that can effectively inhibit LPAAT activation in response to a hypoxia and reoxygenation stimulus.

Compounds

The compound is a small organic molecule that can mimic binding to a complex of enzymes that mediate signal amplification and results in a diminution of intracellular linoleoyl PA levels in response to an inflammatory stimulus. Preferably, the compound is a small organic molecule or a pharmaceutically acceptable salt or hydrate or solvate thereof, wherein said compound can block intracellularlinoleoyl PA formation from lyso-PA, or HODE formation, or inhibit LPAAT activity. Preferably, said compound is a chiral primary or secondary alcohol-substituted heterocyclic compound. The heterocyclic compound contains at least one heterocyclic atom, preferably a nitrogen, within the ring structure, has one to three ring structures with each ring having five to six members. Further the heterocyclic moiety contains a carbonyl carbon atom adjacent to the heterocyclic atom. Most preferably, the heterocyclic moiety is a substituted or unsubstituted xanthine, a substituted or unsubstituted uracil or a substituted or unsubstituted thymine.

Preferably the compound is a resolved R. or S (preferably R) enantiomer of an ω-1 alcohol of a straight chain alkyl ($C_{5-8}$) substituted at the 1-position of 3,7-disubstituted xanthine. The compounds have a xanthine core of the formula:

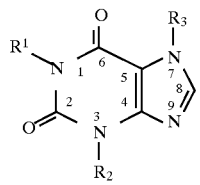

wherein $R_1$ is independently a resolved enantiomer ω-1 secondary alcohol-substituted alkyl ($C_{5-12}$) substantially free of the other enantiomer, and wherein each of $R_2$ and $R_3$ is independently alkyl ($C_{1-12}$) optionally containing one or two nonadjacent oxygen atoms in place of a carbon atom. Preferably $R_1$ is a $C_6$ alkyl with the hydroxyl group as the R enantiomer.

The compound that can inhibit linoleoyl PA in either the sn-1 or sn-2 positions or both can be determined by following an assay procedure described herein. Preferably, the compound is a small organic molecule that can mimic binding to a complex of enzymes that mediate signal amplification. The compounds include resolved enantiomers and/or diastereomers, hydrates, salts, solvates and mixtures thereof, the compounds having a straight or branched aliphatic hydrocarbon structure of formula I:

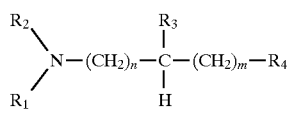

In formula I, n is an integer from one to four and m is an integer from four to twenty. Independently, $R_1$ and $R_2$ are hydrogen, a straight or branched chain alkyl, alkenyl or alkynyl of up to twenty carbon atoms in length or —$(CH_2)_w R_5$. If $R_1$ or $R_2$ is —$(CH_2)_w R_5$, w may be an integer from one to twenty and $R_5$ may be an hydroxyl, halo, $C_{1-8}$ alkoxyl group or a substituted or unsubstituted carbocycle or heterocycle. Alternatively, $R_1$ and $R_2$ may jointly form a substituted or unsubstituted, saturated or unsaturated heterocycle having from four to eight carbon atoms, N being a hetero atom of the resulting heterocycle. $R_3$ may be hydrogen, a hydroxy group, a $C_{1-3}$ straight or branched alkyl, or a $C_{1-3}$ alkoxy.

Preferred compounds may have one of $R_1$ or $R_2$ and $R_3$ that form a substituted or unsubstituted linking carbon chain, having from one to four carbon atoms. This $R_1/R_3$ or $R_2/R_3$ linking chain will join the O and N in a cyclic structure, an integer sum equal to n+a number of carbon atoms in the linking carbon chain being less than six.

In the compounds, a total sum of carbon atoms comprising $R_1$ or $R_2$, $(CH_2)_n$ and $(CH_2)_m$ does not exceed forty. $R_4$ is a terminal moiety comprising a substituted or unsubstituted, heterocyclic moiety, wherein the heterocyclic moiety consists essentially of one to three ring structures having 5–7 members each, a heteroatom, and a predominantly planar structure or essentially aromatic. However, if $R_4$ is phthalimide, m of formula I is not less than five.

The compounds may include resolved enantiomers and/or diastereomers, hydrates, salts, solvates and mixtures thereof that have a straight or branched aliphatic hydrocarbon structure of formula II:

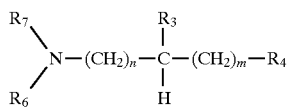

In the above formula II, n, m, $R_3$, and $R_4$ are defined as provided in formula I above. $R_6$ and $R_7$ are hydrogen, a straight or branched chain alkane, alkene or alkyne of up to twenty carbon atoms in length, or —$(CH_2)_xR_8$, at least one of $R_6$ or $R_7$ being —$(CH_2)_xR_8$. In formula II, x is an integer from zero to fourteen and $R_8$ is a moiety having a general structure as provided in formula III

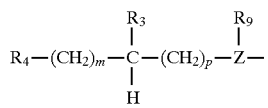

In formula III above, m, $R_3$, and $R_4$ are defined as provided in formula I above. Z is N or CH and p is an integer from zero to four. $R_9$ is H or a straight or branched chain alkane, alkene or alkyne of up to twenty carbon atoms in length.

For example, $R_4$ may be selected from the group consisting of substituted or unsubstituted acridinyl; acridonyl; alkylpyridinyl; anthraquinonyl; ascorbyl; azaazulenyl; azabenzanthracenyl; azabenzanthrenyl; azabenzophenanthrenyl; azachrysenyl; azacyclazinyl; azaindolyl; azanaphthacenyl; azanaphthalenyl; azapyrenyl; azatriphenylenyl; azepinyl; azinoindolyl; azinopyrrolyl; benzacridinyl; benzazapinyl; benzofuryl; benzonaphthyridinyl; benzopyranonyl; benzopyranyl; benzopyronyl; benzoquinolinyl; benzoquinolizinyl; benzotlhiepinyl; benzothiphenyl; benzylisoquinolinyl; biotinyl; bipyridinyl; butenolidyl; butyrolactonyl; caprolactamyl; carbazolyl; carbolinyl; catechinyl; chromenopyronyl; chromonopyranyl; coumarinyl; coumaronyl; decahydroquinolinyl; decahydroquinolonyl; diazaanthracenyl; diazaphenanthrenyl; dibenzazepinyl; dibenzofuranyl; dibenzothiophenyl; dichromylenyl; dihydrofuranyl; dihydroisocoumarinyl; dihydroisoquinolinyl; dihydropyranyl; dihydropyridinyl; dihydropyridonyl; dihydropyronyl; dihydrothiopyranyl; diprylenyl; dioxanthylenyl; enantholactamyl; flavanyl; flavonyl; fluoranyl; fluorescienyl; furadionyl; furanochromanyl; furanonyl; furaoquinolinyl; furanyl; furopyranyl; furopyronyl; heteroazulenyl; hexahydropyrazinoisoquinolinyl; hydrofuranyl; hydrofurnanonyl; hydroindolyl; hydropyranyl; hydropyridinyl; hydropyrrolyl; hydroquinolinyl; hydrothiochromenyl; hydrothiophenyl; indolizidinyl; indolizinyl; indolonyl; isatinyl; isatogenyl; isobenzofurandionyl; isobenzofuranyl; isochromanyl; isoflavonyl; isoindolinyl; isoindolobenzazepinyl; isoindolyl; isoquinolinyl; isoquinuclidinyl; lactamyl; lactonyl; maleimidyl; monoazabenzonaphthenyl; naphthalenyl; naphthimidazopyridinedionyl; naphthindolizinedionyl; naphthodihydropyranyl; naphthofuranyl; naphthothiophenyl; naphthyridinyl; oxepinyl; oxindolyl; oxolenyl; perhydroazolopyridinyl; perhydroindolyl; phenanthraquinonyl; phenanthridinyl; phenanthrolinyl; phthaiideisoquinolinyl; phthalimidyl; phthalonyl; piperidinyl; piperidonyl; prolinyl; pyradinyl; pyranoazinyl; pyranoazolyl; pyranopyrandionyl; pyranopyridinyl; pyranoquinolinyl; pyranopyradinyl; pyranyl; pyrazolopyridinyl; pyridinethionyl; pyridinonaphthalenyl; pyridinopyridinyl; pyridinyl; pyridocolinyl; pyridoindolyl; pyridopyridinyl; pyridopyrimidinyl; pyridopyrrolyl; pyridoquinolinyl; pyronyl; pyrrocolinyl; pyrrolidinyl; pyrrolizidinyl; pyrrolizinyl; pyrrolodiazinyl; pyrrolonyl; pyrrolopyrimidinyl; pyrroloquinolonyl; pyrrolyl; quinacridonyl; quinolinyl; quinolizidinyl; quinolizinyl; quinolonyl; quinuclidinyl; rhodaminyl; spirocoumaranyl; succinimidyl; sulfolanyl; sulfolenyl; tetrahydrofuranyl; tetrahydroisoquinolinyl; tetrahydropyranyl; tetrahydropyridinyl; tetrahydrothiapyranyl; tetrahydrothiophenyl; tetrahydrothiopyranonyl; tetrydrothiopyranyl; tetronyl; thiabenzenyl; thiachromanyl; thiadecalinyl; thianaphthenyl; thiapyranyl; thiapyronyl; thiazolopyridinyl; thienopryidinyl; thienopyrrolyl; thienothiophenyl; thiepinyl; thiochromenyl; thiocoumarinyl; thiophenyl; thiopyranyl; triazaanthracenyl; triazinoindolyl; triazolopyridinyl; tropanyl; xanthenyl; xanthonyl; xanthydrolyl; adeninyl; alloxanyl; alloxazinyl; anthranilyl; azabenzanthrenyl; azabenonaphthenyl; azanaphthacenyl; azaphenoxazinyl; azapurinyl; azinyl; azoloazinyl; azolyl; barbituric acid; benzazinyl; benzimidazolethionyl; benzimnidazolonyl; benzimidazolyl; benzisothiazolyl; benzisoxazolyl; benzocinnolinyl; benzodiazocinyl; benzodioxanyl; benzodioxolanyl; benzodioxolyl; benzopyridazinyl; benzothiazepinyl; benzothiazinyl; benzothiazolyl; benzoxazinyl; benzoxazolinonyl; benzoxazolyl; cinnolinyl; depsidinyl; diazaphenanthrenyl; diazepinyl; diazinyl; dibenzoxazepinyl; dihydrobenzimidazolyl; dihydrobenzothiazinyl; dihydrooxazolyl; dihydropyridazinyl; dihydropyrimidinyl; dihydrothiazinyl; dioxanyl; dioxenyl; dioxepinyl; dioxinonyl; dioxolanyl; dioxolonyl; dioxopiperazinyl; dipyrimidopyrazinyl; dithiolanyl; dithiolenyl; dithiolyl; flavinyl; furopyrimidnyl; glycocyarnidinyl; guaninyl; hexahydropyrazinoisoquinolinyl; hexahydropyridazinyl; hydantoinyl; hydroimidazolyl; hydropyrazinyl; hydropyrazolyl; hydropyridazinyl; hydropyrimidinyl; imidazolinyl; imidazolyl; imidazoquinazolinyl; imidazothiazolyl; indazolebenzopyrazolyl; indoxazenyl; inosinyl; isoalloxazinyl; isothiazolyl; isoxazolidinyl; isoxazolinonyl; isoxazolinyl; isoxazolonyl; isoxazolyl; lumazinyl; methylthyminyl; methyluracilyl; morpholinyl; naphtiridazolyl; oroticyl; oxathianyl; oxathiolanyl; oxazinonyl; oxazolidinonyl; oxazolidinyl; oxazolidonyl; oxazolinonyl; oxazolinyl; oxazolonyl; oxazolopyrimidinyl; oxazolyl; perhydrocinnolinyl; perhydropyrroloazinyl; perhydropyrrolooxazinyl; perhydropyrrolothiazinyl; perhydrothiazinonyl; perimidinyl; phenazinyl; phenothiazinyl; phenoxathiinyl; phenoxazinyl; phenoxazonyl; phthalazinyl; piperazindionyl; piperazinodionyl; polyquinoxalinyl; pteridinyl; pterinyl; purinyl; pyrazinyl; pyrazolidinyl; pyrazolidonyl; pyrazolinonyl; pyrazolinyl; pyrazolobenzodiazepinyl; pyrazolonyl; pyrazolopyridinyl; pyrazolopyrimidinyl; pyrazolotriazinyl; pyrazolyl; pyridazinyl; pyridazonyl; pyridopyrazinyl; pyridopyrimidinyl; pyrimidinethionyl; pyrimidinyl; pyrimidionyl; pyrimidoazepinyl; pyrimidopteridinyl; pyrrolobenzodiazepinyl; pyrrolodiazinyl; pyrrolopyriridinyl; quinazolidinyl; quinazolinonyl; quinazolinyl; quinoxalinyl; sultamyl; sultinyl; sultonyl; tetrahydrooxazolyl; tetrahydropyrazinyl; tetrahydropyridazinyl; tetrahydroquinoxalinyl; tetrahydrothiazolyl; thiazepinyl; thiazinyl; thiazolidinonyl; thiazolidinyl; thiazolinonyl; thiazolinyl; thiazolobenzimidazolyl; thiazolyl; thienopyrimidinyl; thiazolidinonyl; thyminyl; triazolopyrimidinyl; uracilyl; xanthinyl; xylitolyl, azabenzonaphthenyl; benzofuroxanyl; benzothadiazinyl; benzotriazepinonyl; benzotriazolyl; benzoxadizinyl; dioxadiazinyl; dithiadazolyl; dithiazolyl; furazanyl; furoxanyl; hydrotriazolyl; hydroxytnzinyl; oxadiazinyl; oxadiazolyl; oxathiazinonyl; oxatriazolyl; pentazinyl; pentazolyl; petrazinyl; polyoxadiazolyl; sydononyl; tetraoxanyl; tetrazepinyl; tetrazinyl; tetrazolyl; thiadiazinyl; thiadiazolinyl; thiadiazolyl; thiadioxazinyl; thiatriazinyl; thiatriazolyl; thiatriazolyl; triazepinyl; triazinoindolyl; triazinyl; triazolinedionyl; triazolinyl; triazolyl; trioxanyl; triphenodioxazinyl; triphenodithiazinyl; trithiadiazepinyl; trithianyl; trixolanyl.

In these compounds, the most preferred ring systems ($R_4$) include, for example, dimethylxanthinyl, methylxanthinyl, phthalimidyl, homophthalimidyl, methylbenzoyleneureayl, quinazolinonyl, octylcarboxamidobenzenyl, methylbenzamidyl, methyldioxotetrahydropteridinyl, glutarimidyl, piperidonyl, succinimidyl, dimethoxybenzenyl, methyldihydrouracilyl, methyluracilyl, methylthyminyl, piperidinyl, dihydroxybenzenyl, or methylpurinyl, even more preferably, methylxanthinyl, dimethylxanthinyl or a derivative thereof.

Specific compounds that have activity to treat or prevent the manifestations of hypoxic tissue injury and are LPAAT inhibitors include compounds listed below.

TABLE 1

R-1-(5-hydroxyhexyl)-3,7-dimethylxanthine (Lisofylline)
N-(11-octylamino-10-hydroxyundecyl)-homophthalimide
N-(11-octylamino-10-hydroxyundecyl)-3-methylxanthine
N-(11-octylamino-10-hydroxyundecyl)-2-piperdone
3-(11-octylamino-10-hydroxyundecyl)-1-methyluracil
3-(11-octylamino-10-hydroxyundecyl)-1-methyldihydrouracil
1-(9-decylamino-8-hydroxynonyl)-3,7-dimethylxanthine
1-(9-dodecylamino-8-hydroxynonyl)-3,7-dimethylxanthine
1-(11-hexylamino-8-hydroxyundecyl)-3,7-dimethylxanthine
N-(11-phenylamino-10-hydroxundecyl)-3,7-dimethylxanthine
1-(9-(2-hydroxydecyl-1-amino)nonyl)-3,7-dimethylxanthine
N-(9-Octylamino-8-hydroxynonyl)phthalimide

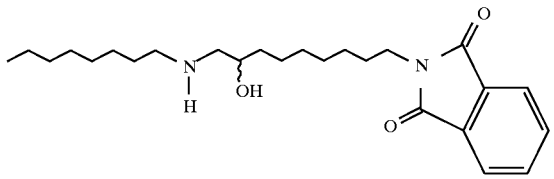

N-(11-Octylamino-10-hydroxyundecyl)homophthalimide

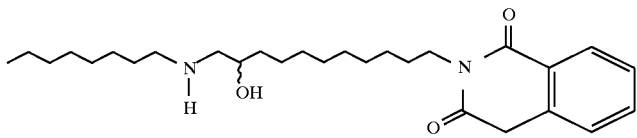

1-(5-hydroxy-6-(N-benzyl)aminohexyl)-3-methylbenzoyleneurea

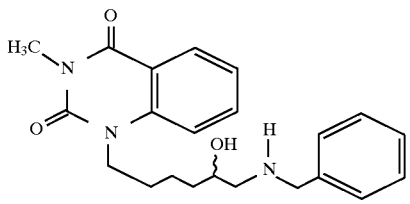

3-(11,10-Oxidoundecyl)quinazoline-4(3H)-one

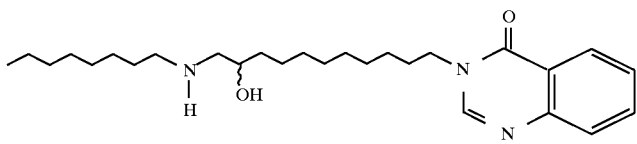

$N^2$-(5-hydroxy-6-($N^3$-propyl)aminohexyl)-($N^1$-propyl)glutaramide

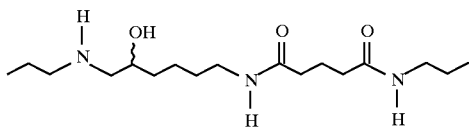

2-(11-Octylamino-10-hydroxyundeclcarboxamido)-octylcarboxamidobenzyl

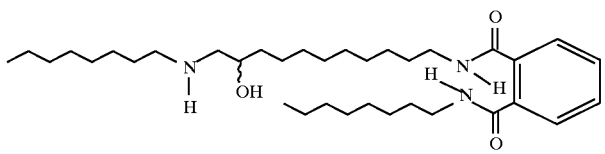

TABLE 1-continued
1-Octylamino-2,11-undecadiol
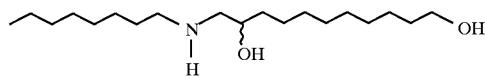
1-(9-Octylamino-8-hdroxynonyl)-3-methylxanthine
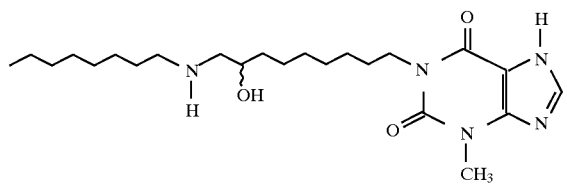
1-(9-Tetradecylamino-8-hydroxynonyl)-3-methylxanthine
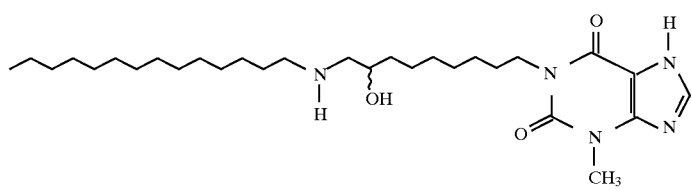
1-(11-Octylamino-10-hydroxyundecyl)-3-methylxanthine
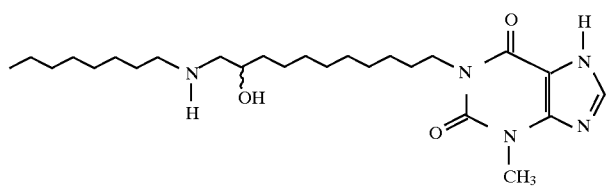
7-(11-Octylamino-10-hydroxyundecyl)-1,3-dimethylxanthine
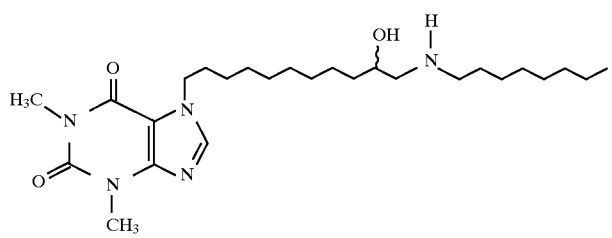
1-(11,10-Octylamino-10-hydroxyundecyl)-1-methyl-2,4-dioxotetrahydropteridine
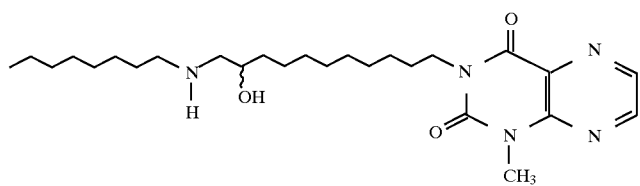
1-(5-hydroxy-6-(N-benzyl)aminohexyl)-3,7-dimethylxanthine
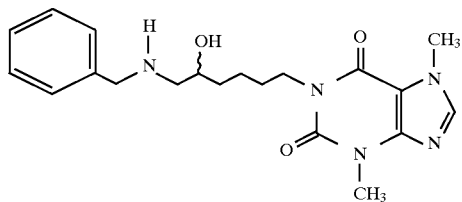

TABLE 1-continued
1-(5-hydroxy-6-(N-propyl)aminohexyl)-3,7-dimethylxanthine
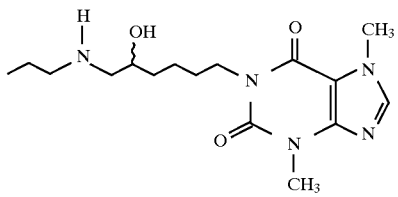
N-(11-Ocytlamino-10-hydroxyundecyl)glutarimide
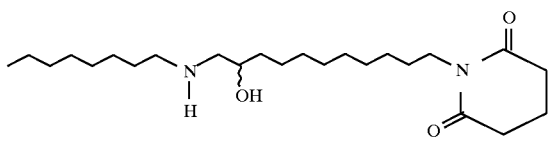
N-(11-Octylamino-10-hydroxyundecyl)-2-piperidone
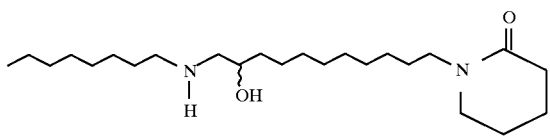
N-(11-Octylamino-10-hydroxyundecyl)succinimide
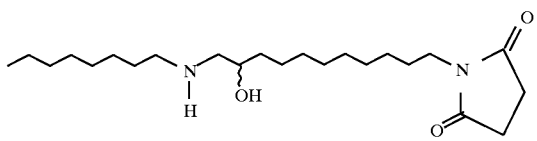
2-(11-Octylamino-10-hydroxyundecyl)-1,3-dimethoxybenzene
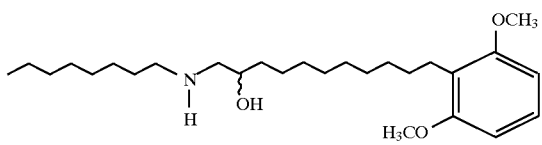
3-(5-hydroxy-6-(N-propyl)aminohexyl)-1-methyluracil
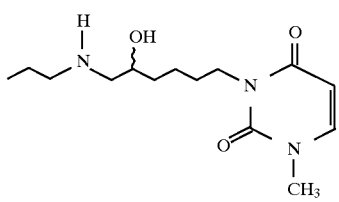
3-(9-Octylamino-8-hydroxynonyl)-1-methyluracil
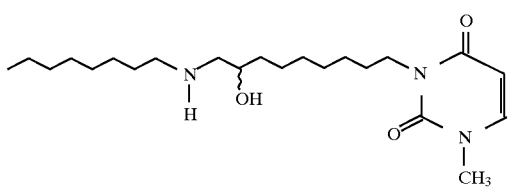

TABLE 1-continued
3-(11-Octylamino-10-hydroxyundecyl)-1-methyluracil
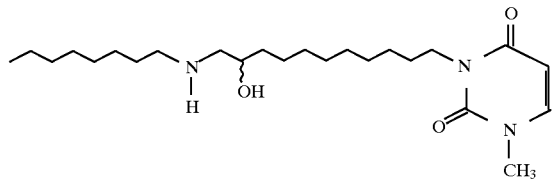
3-(11-Octylamino-10-hydroxyundecyl)-1-methyldihydrouracil
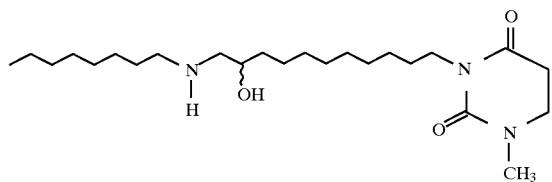
3-(8-Octylamino-9-hydroxynonyl)-1-methylthymine
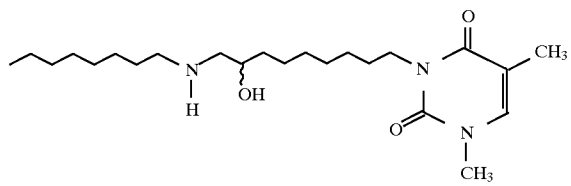
3-(5-hydroxy-6-(N-undecyl)aminohexyl)-1-methylthymine
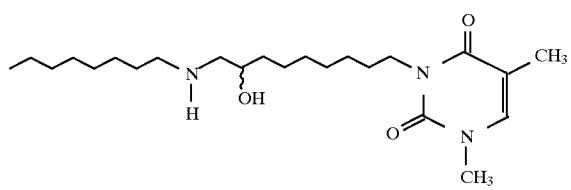
3-(11-Octylamino-10-hydroxyundecyl)-1-methylthymine
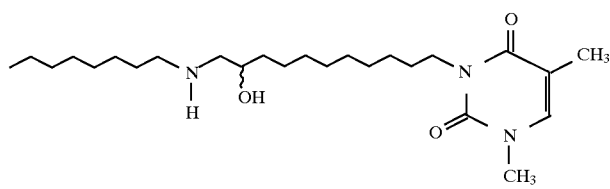
3-(6-Propylamino-5-hydroxyhexyl)-1-methylthymine
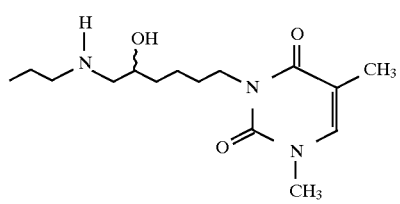

TABLE 1-continued
1-(8-hydroxy-9-(N-benzyl)aminononyl)-3,7-dimethylxanthine
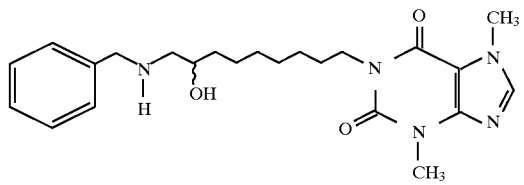
1-(5-hydroxy-6-(N-octyl)aminohexyl)-3,7-dimethylxanthine
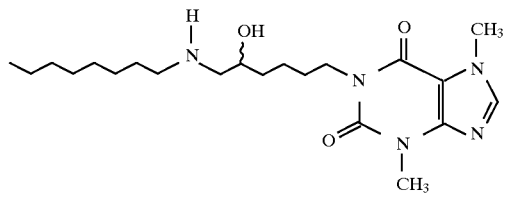
1-(5-hydroxy-6-(N-(4-phenyl)butyl)aminohexyl)-3,7-dimethylxanthine
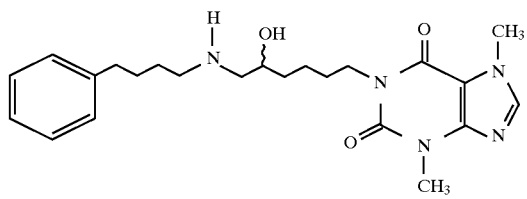
1-(6-Undecylamino-5-hydroxyhexyl)-3,7-dimethylxanthine
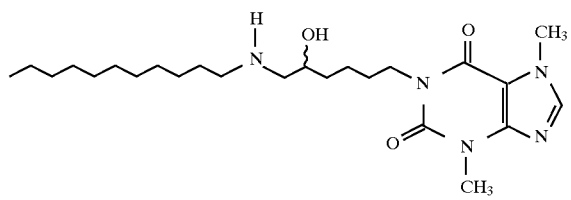
1-(5-hydroxy-6-(N-cyclohexylmethyl)aminohexyl)-3,7-dimethylxanthine
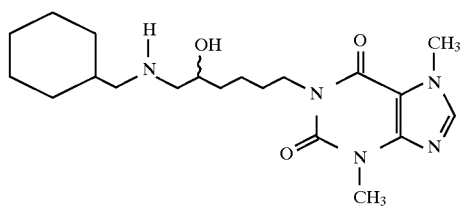
1-(5-hydroxy-6-(N-(6-hydroxy)hexyl)aminohexyl)-3,7-dimethylxanthine
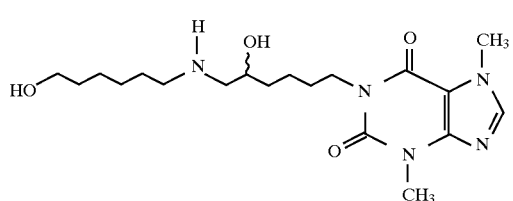

TABLE 1-continued
1-(5-hydroxy-6-(N,N-dihexyl)aminohexyl)-3,7-dimethylxanthine
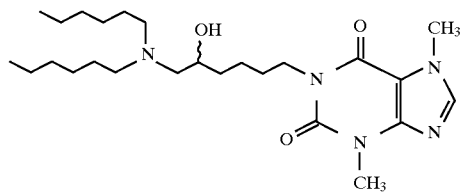
1-(5-hydroxy-6-(N-(4-methoxy)benzyl)aminohexyl)-3,7-dimethylxanthine
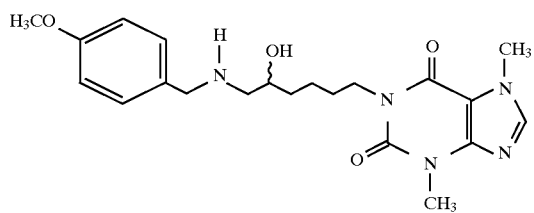
1-(8-hydroxy-9-(N-octyl)aminononyl)-3,7-dimethylxanthine
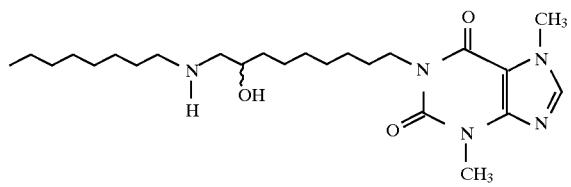
1-(5-hydroxy-6-(N-tetradecyl)aminohexyl)-3,7-dimethylxanthine
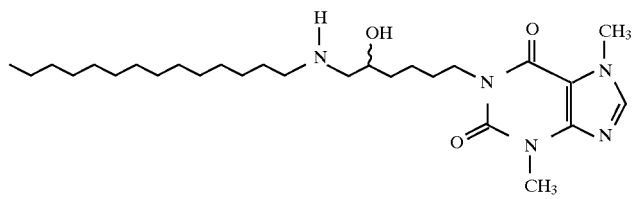
1[6-(Cyclopropylmethylamino)-5-hydroxyhexyl)]-3,7-dimethylxanthine
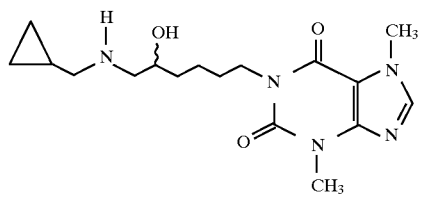
1-(6-Decylamino-5-hydroxyhexyl)-3,7-dimethylxanthine
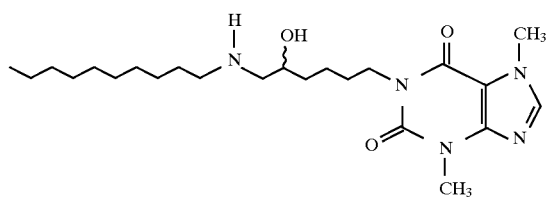

TABLE 1-continued
1-(6-Dodecylamino-5-hydroxyhexyl)-3,7-dimethylxanthine
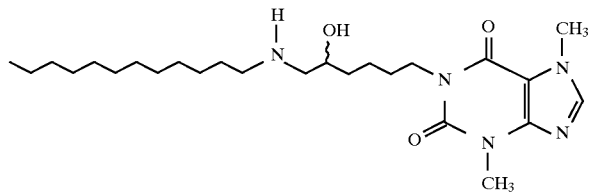
1-(11-Benzylamino-10-hydroxyundecyl-3,7-dimethylxanthine
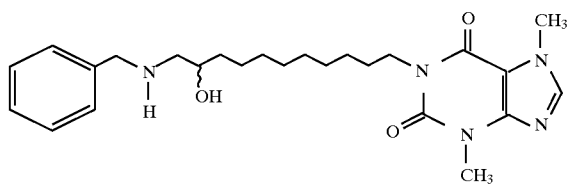
1-(9-Decylamino-8-hydroxynonyl)-3,7-dimethylxanthine
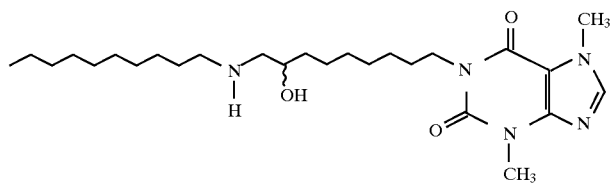
1-(9-Tetradecylamino-8-hydrononyl)-3,7-dimethylxanthine
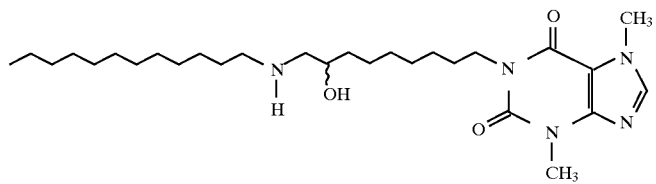
1-(9-Tetradecylamino-8-hydroxynonyl)-3,7-dimethylxanthine
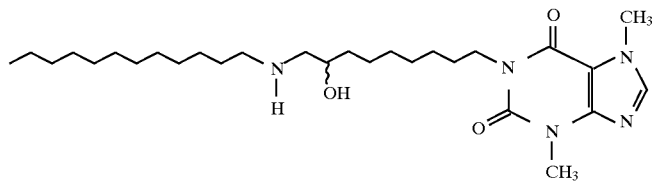
1-(11-Hexylamino-10-hydroxyundecyl)-3,7-dimethylxanthine
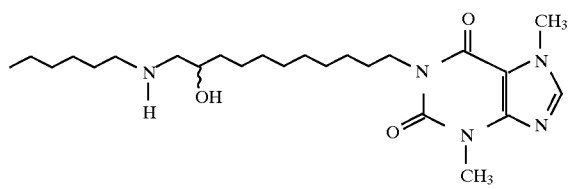

TABLE 1-continued
1-(11-Octylamino-10-hydroxyundecyl-3,7-dimethylxanthine
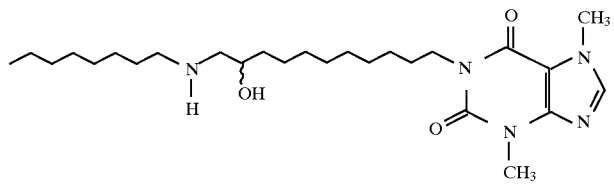
1-(6-Allylamino-5-hydroxyhexyl)-3,7-dimethylxanthine
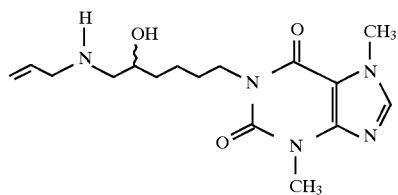
1-(11-Allylamino-10-hydroxyundecyl)-3,7-dimethylxanthine
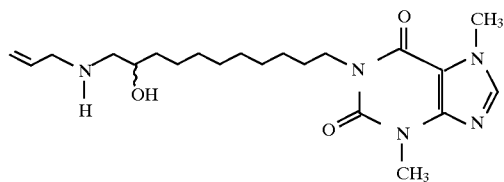
1-(6-N-Methyloctadecylamino-5-hydroxyhexyl)-3,7-dimethylxanthine
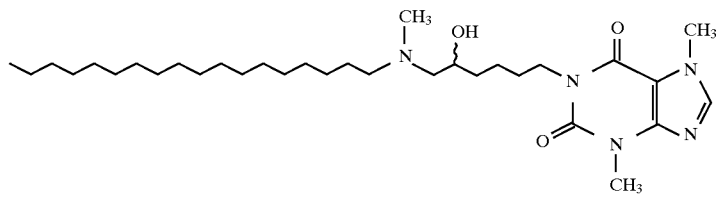
1-(11-Decylamino-10-hydroxyundecyl)-3,7-dimethylxanthine
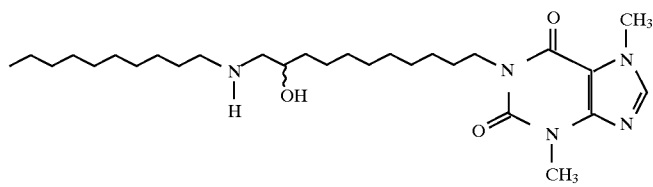
1-(11-Dodecylamino-10-hydroxyundecyl)-3,7-dmethylxanthine
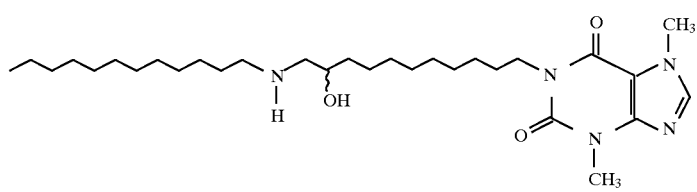

TABLE 1-continued 1-(11-Tetradecylamino-10-hydroxyundecyl)-3,7-dimethylxanthine

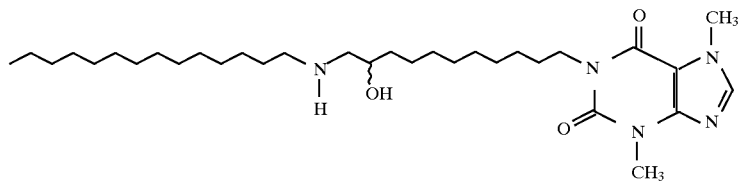

1-[11-(4-Fluorobenzylamino)-10-hydroxyundecyl]-3,7-dimethylxanthine

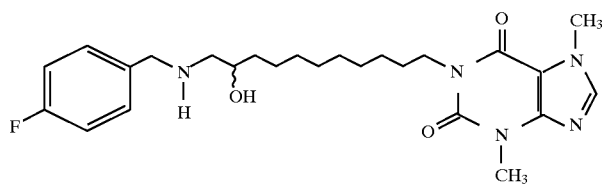

1-[11-(4-Trifluoromethylbenzylamino)-10-hydroxyundecyl]3,7-dimethylxanthine

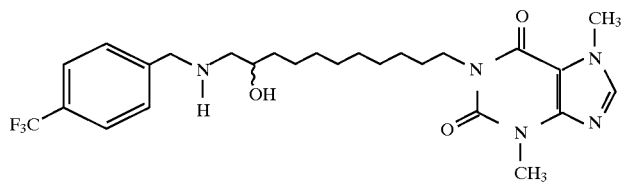

1-{11-(3-Diethylaminopropylamino)-10-hydroxyundecyl]-3,7-dimethylxanthine

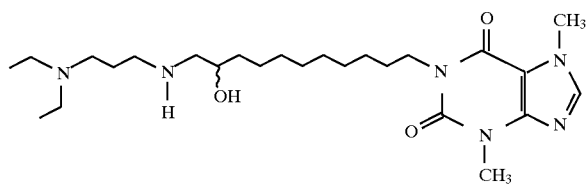

N,N'-bis[(10-yl-9-hydroxydecyl)-3,7-dimethylxanthine]diaminododecane

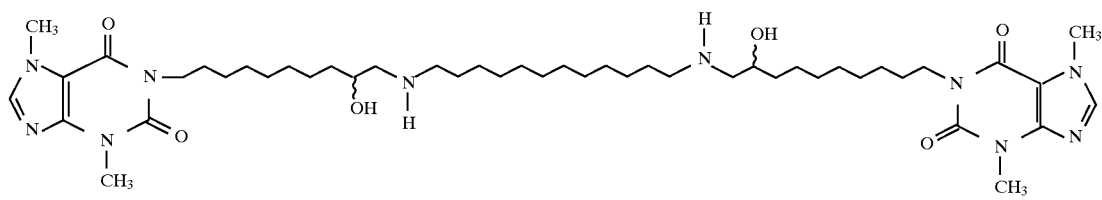

1-(14-Bromo-13-hydroxytetradecyl)-3,7-dimethylxanthine

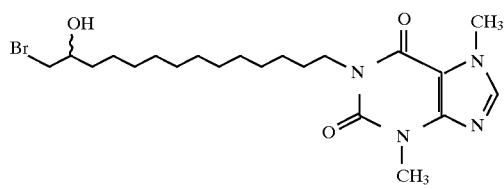

TABLE 1-continued
1-[11-(4-Aminobenzylamino)-10-hydroxyundecyl]-3,7-dimethylxanthine
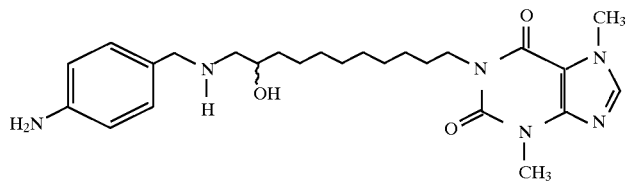
1-[11-(3,4,5-Trimethoxybenzylamino)-10-hydroxyundecyl]-3,7-dimethylxanthine
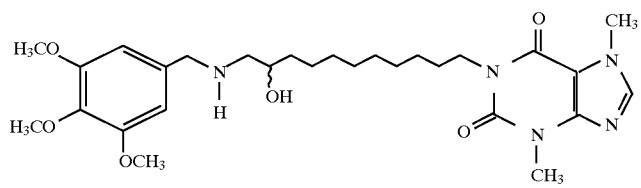
1-[11-(3-Butoxypropylamino)10-hydroxyundecyl}3,7-dimethylxanthine
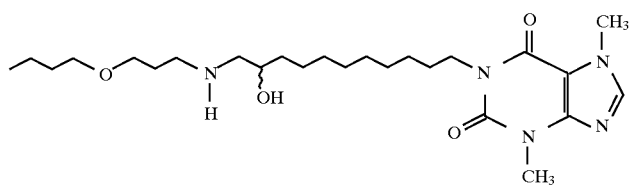
1-(14-Ocytlamino-13-hydroxytetradecyl]-3,7-dimethylxanthine
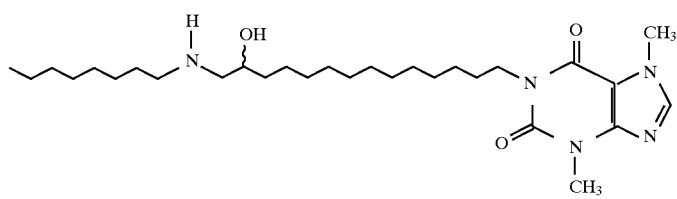
1-(11-Propylamino-10-hydroxyundecyl)-3,7-dimethylxanthine
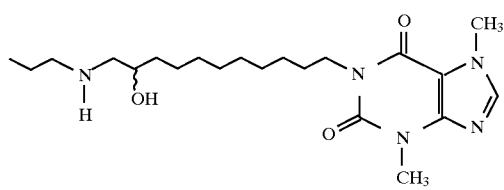
1-(1-Undecylamino-10-hydroxydecyl-3,7-dimethylxanthine
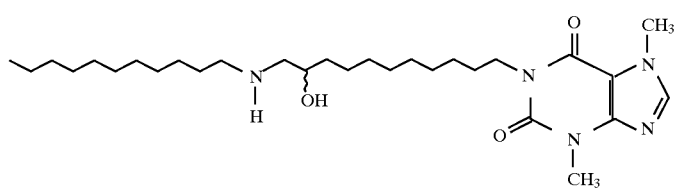

TABLE 1-continued
1-(11-Phenylamino-10-hydroxyundecyl)-3,7-dimethylxanthine
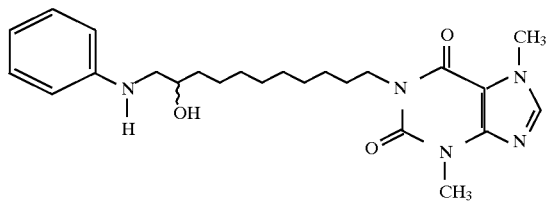
N,N-bis[11-yl-10-hydroxyundecyl)-3,7-dimethylxanthine]undecylamine
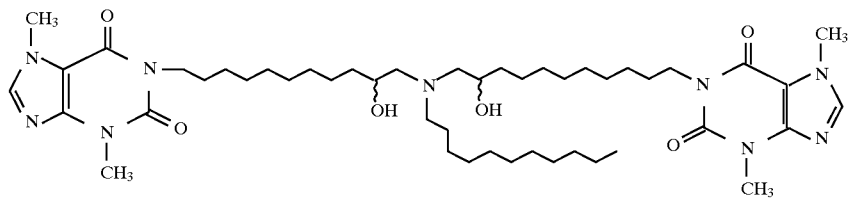
1-(11-Octadecylamino-10-hydroxyundecyl)-3,7-dimethylxanthine
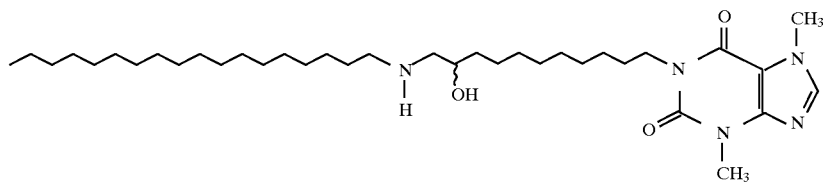
1-[9-(N-Mehtyloctylamino-8-hydroxynonyl)]-3,7-dimethylxanthine
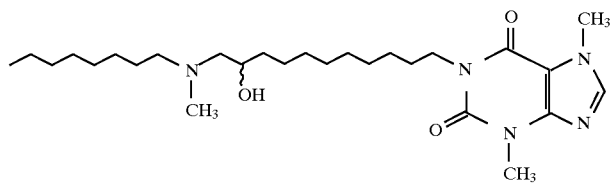
1-(4-Tetradecylamino-3-hydroxybutyl)-3,7-dimethylxanthine
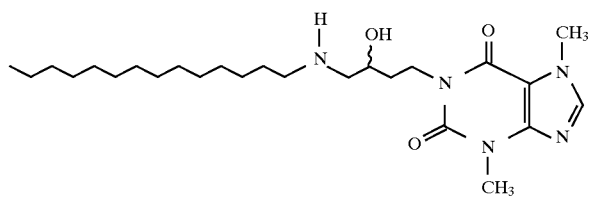
1-[9-(2-hydroxydecyl-1-amino)nonyl)-3,7-dimethylxanthine
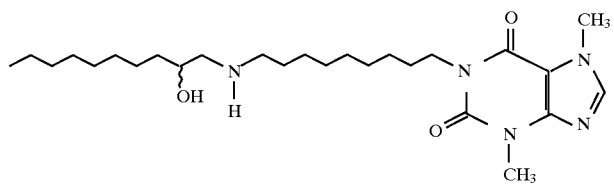

TABLE 1-continued 1-(6-Octadecylamino-5-hydroxyhexyl)-3,7-dimethylxanthine

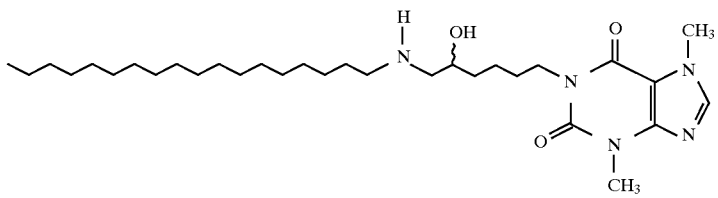

1-[11-(N-Octylacetamido)10-hydroxyundecyl]-3,7-dimethylxanthine

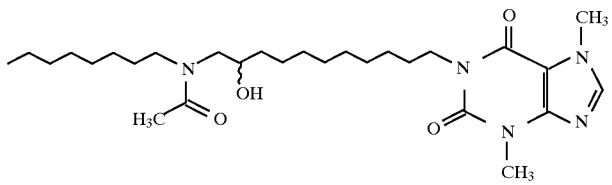

11-Octylamino-10-hydroxyundecanoic acid amide

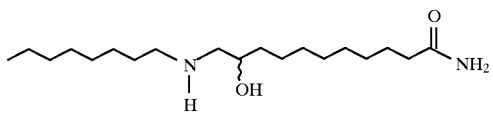

2-(11-Octylamino-10-hydroxyundecyl)-N-methylbenzamide

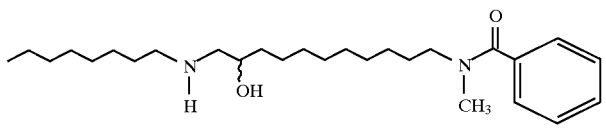

1-{11-(N-Methyl-N-octylamino)-10-hydroxyundecyl}-3,7-dimethylxanthine

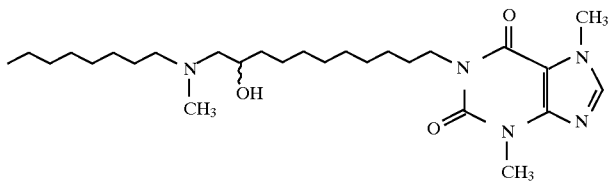

Linoleoyl PA Assay

This procedure begins with those cells that would respond to hypoxic cell injury and reoxygenation by releasing or responding to inflammatory cytokines. Such cells include macrophage and fibroblastic cells. Examples of appropriate macrophage cell lines include, U937, THP1, U1, and P288s (available from standard sources, such as ATCC). The cells are stimulated with a stimulant with or without a candidate drug. Examples of stimulants include 3–5% serum, such as fetal calf serum, or tumor necrosis factor (TNF)(e.g., 20 ng/ml) both of which are standard laboratory reagents, or by keeping the cells in a $CO_2$ atmosphere before transferring them back to an $O_2$ atmosphere. After a time course (within 5 minutes, preferably within 1 minute), the cells are immersed in ice cold methanol to stop any cellular signaling reactions.

One must first quantitatively and qualitatively separate PAs from the other lipids found in serum by a chemical extraction of lipids and high performance liquid chromatography (HPLC) to separate and detect PAs. Chemical extraction can be accomplished, for example, by the method of Bligh et al. (*Canadian J. Biochem. Physiol.* 37:914–917, 1959) or that of Folch et al. (*J. Biochem.* 226:497–509, 1957). Briefly, the method of Bligh et al. involves an organic extraction of lipids from biological tissue homogenates or fluids. One volume of sample and three volumes of methanol:chloroform (2:1) are vigorously shaken for 2 min. One volume of chloroform is added and then shaken vigorously for 30 sec. One volume of water is added and then shaken vigorously for 30 sec. The mixture is filtered and the upper aqueous layer is discarded. The lower organic layer contains a mixture of lipid classes. The method of Folch et al. involves the extraction of lipids from biological tissue homogenates or body fluids. One volume of sample plus 20 volumes of chloroform:methanol (2:1) are vigorously shaken for 2 min. The mixture is filtered and an amount of 0.1N KCl equal to 20% of the extraction mixture volume is added and the mixture is shaken vigorously for 2 min. The aqueous and organic phases are allowed to separate. The upper aqueous layer is discarded. The lower organic layer contains a mixture of lipid classes. Free fatty acids and neutral lipids can be separated from phospholipids by normal phase high performance liquid chromatography (HPLC) by modifying the method of Van Kessel et al. (*Biochim et Biophys Acta* 486:524–530, 1977). This method involves separation of lipids into their major classes by normal phase (silica) high performance liquid chromatography (HPLC). A 5 micron, 25 cm×0.45 cm silica HPLC column is connected to a binary solvent delivery system followed with a UV detector. The lipid sample is injected on the column and a solvent gradient is run at 1.0 ml/min. The solvent gradient is hexane:isopropanol:water in the proportions 3:4:0.75 run isocratically for 3 min, then ramped to hexane:isopropanol:water in the proportions 3:4:1.4 in 15 min, then run isocratically at the same proportions for 15 min. Detection is at 206 nm. The PAs run at about 6–8 min when run at 1 ml/min when run in hexane:isopropanol (3:4).

Once the PA peak is identified and isolated, it is subject to general alkaline hydrolysis or another method to isolate the FFAs (free fatty acids) from the PA species. This assay is based upon identifying linoleoyl PA species in particular such that the identity of the acyl side chains of PA species in stimulated cells is critical for determining if a candidate compound is effective for inhibiting host cell signaling in cells stimulated by inflammatory cytokines in response to hypoxic/reperfusion injury. The FFAs are isolated after hydrolysis.

Figure 8:
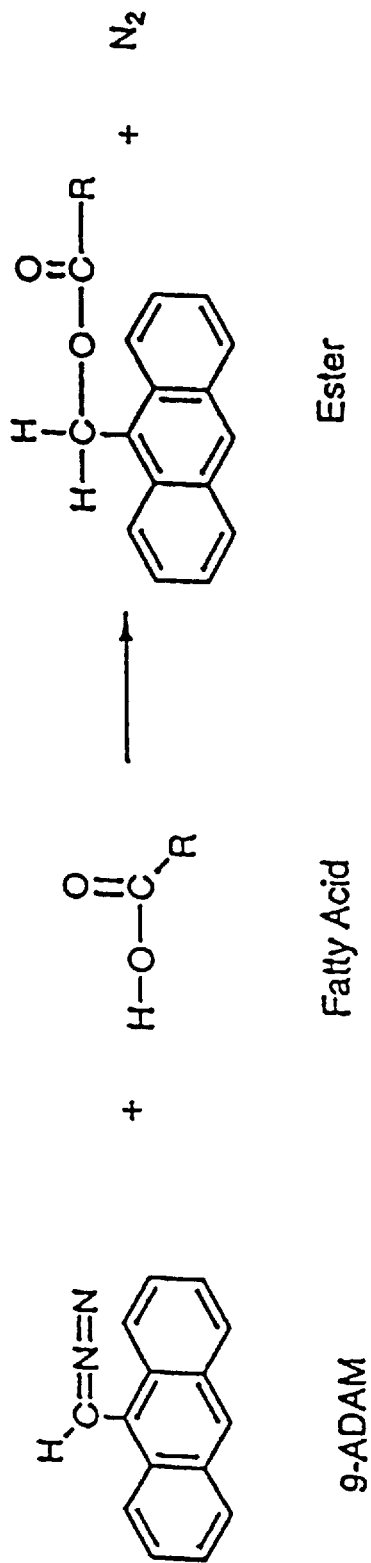
FIG. 8 illustrates the chemistry of a reaction to derivatize FFAs (free fatty acids) with 9-ADAM.

The isolated FFAs are derivatized into fatty acid derivatives of 9-anthroyl diazomethane (9-ADAM), which absorbs light at 254 nm and fluoresces with emission at 410 nm. FFA derivatives were prepared essentially according to the method described in Nakaya et al. (*Bull. Chem. Soc. Japan* 40:691–692, 1967, and Yoshida et al., *Analytical Biochem.* 173:70–74, 1988). The derivatization is based on the reaction shown in FIG. 8. Briefly, 9-anthraldehyde hydrazone for 9-anthroyl diazomehane derivatization was synthesized from 9-anthraldehyde and hydrazine monohydrate as follows: (a) 8.8 g 9-anthraldehyde (Aldrich Milwaukee, Wis.) was dissolved in 150 mL absolute ethanol and 8 mL hydrazine monohydrate (Aldrich Milwaukee, Wis.) was added dropwise with continual stirring. (b) The mixture cleared as hydrazine was added then turned opaque as the last drops were added. (c) The reaction was stirred at room temperature for 3 hr, then was filtered (Whatman #1 filter paper, Whatman Int. Maidstone UK) and dried. (d) The product was recrystalized twice with absolute ethanol. (e) The yield was 3.1 g of needle-like crystals.

Figure 9:
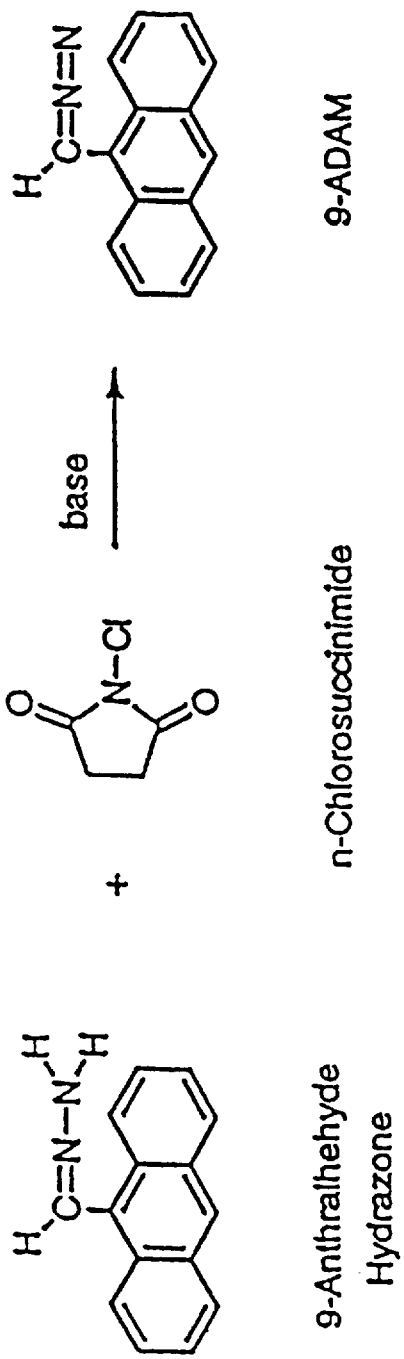
FIG. 9 illustrates the chemistry of a reaction to make a 9-ADAM derivatizing reagent.

The following solutions were made in ethyl acetate: 9-anthraldehyde hydrazone (0.0276M, 0.0304 g/5 mL), Quinuclidine (0.2760M, 0.1534 g/5 mL (oxidizing reagent)), and N-chlorosuccinimide (0.0276M, 0.0184 g/5 mL (catalyst)). Equal volumes of these solutions were mixed to react at room temperature for 30 min. The resulting 9-anthryl diazomethane (9-ADAM) was unstable and was made fresh daily. This reaction is shown in FIG. 9.

The derivatizing reaction was carried out by diluting 50 μL of each FFA standard to 200 μL with methanol. FFA standards (1.0 mg/mL) were made up in methanol using: Heptadecanoic acid 17:0 (Aldrich Chemical Milwaukee, Wis.); Arachidonic acid 20:4 (Matreya, Inc., Pleasant Gap, Pa.); Linoleic acid 18:2 (Matreya, Inc., Pleasant Gap, Pa.); Linolenic acid 18:3 (Matreya, Inc., Pleasant Gap, Pa.); Palmitic acid 16:0 (Matreya, Inc., Pleasant Gap, Pa.); Oleic acid 18:1 (Matreya, Inc., Pleasant Gap, Pa.); Stearic acid 18:0 (Matreya, Inc., Pleasant Gap, Pa.); Myristic acid 14:0 (Matreya, Inc., Pleasant Gap, Pa.); Lauric acid 12:0 (Matreya, Inc., Pleasant Gap, Pa.); Arachidic acid 20:0 (Matreya, Inc., Pleasant Gap, Pa.); and n-Docosanoic acid 22:0 (Matreya, Inc., Pleasant Gap, Pa.). Derivatizing solution (200 μL) was added. The mixture was reacted for 1 hr at room temperature to form each derivatized standard. 20 μL was injected into an HPLC and run by a reverse phase method described below.

A reverse phase HPLC procedure used to separate and quantitate the derivatized anthroyl FFAs. A reverse phase "C8" column (4.6 cm×25 cm, 5 micron Spherisorb® C8, Alltech Associates, Inc. Deerfield, Ill.) separated the saturated FFAs, and a reverse phase "C18" column (4.6 mm×15 cm, 3 micron Spherisorb® ODS2 Alitech Associates, Inc. Deerfield, Ill.) separated the unsaturated FFAs. Neither column individually could resolve all the derivatized FFA standards. To solve the problem, a 3 micron, 15 cm "C18" column was connected to the HPLC followed by a 5 micron, 25 cm "C8" column. The high performance liquid chromatograph was a model 517 from Gilson Medical Electronics, Inc., Middleton, Wis. Two detectors were connected in tandem. The first was Model UVIS 200 from Linear Instruments, Reno, Nev. The second was Model 121 Fluorometer from Gilson Medical Electronics.

Table 2 below shows the chromatographic conditions used.

TABLE 2

| | |
|---|---|
| UV Detection: | 254 nm |
| Fluorescent Detection: | Excitation: 305–395 nm bandpass filter |
| | Emission: 430–470 nm bandpass filter |
| Buffer A: | 70% Acetonitrile: 30% $H_2O$ |
| Buffer B: | 100% Acetonitrile |
| Flow: | 1.0 mL per min |
| Gradient: | 40% B for 2 min |
| | from 40% to 45% B in 18 min |
| | from 45% to 54% B in 10 min |
| | from 54% to 70% B in 5 min |
| | from 70% to 94% B in 19 min |
| | from 94% to 99% B in 1 min |
| | 99% B for 29 min |
| | from 99% to 40% B in 1 min |
| | 40% B for 5 min |

The foregoing method was used to correlate the intracellular mechanisms of cell signaling inhibition of the exemplary compounds with the predictive in vitro and in vivo data in general and the ability to prevent ARDS and MOD (multiple organ dysfunction)in.particular.

Formulation and Dosage

It will be recognized by one of skill in the art that the form and character of the pharmaceutically acceptable carrier or diluent is dictated by the amount of active ingredient with which it is to be combined, the route of administration and other well-known variables. An amino alcohol or chiral secondary alcohol compound or a pharmaceutically acceptable salt or hydrate or solvate thereof is administered to a patient in an amount sufficient to treat or prevent a hypoxic-mediated disease. An amino alcohol or chiral primary or secondary alcohol compound, or a pharmaceutically acceptable salt or hydrate or solvate thereof, can be administered to such human in a conventional dosage form prepared by combining the amino alcohol or chiral primary or secondary alcohol compound or a pharmaceutically acceptable salt or hydrate or solvate thereof, with a conventional pharmaceutically acceptable carrier or diluent according to known pharmaceutical formulation techniques. The route of administration of the compound (e.g., amino alcohol or chiral primary or secondary alcohol-substituted heterocyclic compound) is not critical but is usually oral or parenteral, preferably parenteral to the site of injury. The term parenteral, as used herein, includes intravenous, intramuscular, subcutaneous, intranasal, intrarectal, transdermal, opthalmic, intravaginal or intraperitoneal administration. The subcutaneous and intramuscular forms of parenteral administration are generally preferred. The daily parenteral dosage regimen will preferably be from about 0.01 mg/kg to about 25 mg/kg of total body weight, most preferably from about 0.1 mg/kg to about 4 mg/kg. Preferably, each parenteral dosage unit will contain the active ingredient in an amount of from about 0.1 mg to about 400 mg. The compounds are generally active when given orally and can be formulated as liquids, for example, syrups, suspensions or emulsions, tablets, capsules and lozenges. A liquid formulation will generally consist of a suspension or solution of the compound or pharmaceutically acceptable salt in a suitable liquid carrier(s), for example, ethanol, glycerine, non-aqueous solvent, for example polyethylene glycol, oils, or water with a suspending agent, preservative, flavoring or coloring agent. A composition in the form of a tablet can be prepared using any suitable pharmaceutical carrier(s) routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into a hard gelatin capsule. Alternatively, a dispersion or suspension can be prepared using any suitable pharmaceutical carrier(s), for example, aqueous gums, celluloses, silicates or oils and the dispersion or suspension then filled into a soft gelatin capsule. The daily oral dosage regimen will preferably be from about 0.01 mg/kg to about 40 mg/kg of total body weight. Preferably, each oral dosage unit will contain the active ingredient in an amount of from about 0.1 mg to about 1000 mg.

It will be recognized by one of skill in the art that the optimal quantity and spacing of individual dosages of a compound or a pharmaceutically acceptable salt or hydrate or solvate thereof will be determined by the nature and extent of the condition being treated, the form, route and site of administration, and the particular patient being treated, and that such optimums can be determined by conventional techniques. It will also be appreciated by one of skill in the art that the optimal course of treatment (i.e., the number of doses of a compound or a pharmaceutically acceptable salt or hydrate or solvate thereof given per day and duration of therapy) can be ascertained by those skilled in the art using conventional course of treatment determination tests.

Without further elaboration, it is believed that one skilled in the art can, using the preceding description, utilize the present invention to its fullest extent. The following examples are, therefore, to be construed as merely illustrative and not a limitation of the scope of the present invention in any way.

EXAMPLE 1

This example illustrates a study of Lisofylline in a murine hemorrhage and resuscitation model. Male Balb/C mice, 8–12 weeks of age, were obtained from Harlan-Sprague Dawley (Indianapolis, Ind.). The animals were kept on a 12 hour light/dark cycle with free access to food and water. With this model, 30% of the calculated blood volume (approximately 0.55 ml for a 20 gram mouse) was withdrawn from a methoxyflurane anesthetized mouse by cardiac puncture over a 60-second period. The blood was collected into a heparinized syringe (5 units heparin), kept at 37° C. for one hour, then reinfused into the mouse through a retroorbital plexus injection. Using this method, one is able to resuscitate all hemorrhaged mice without complication. The total period of methoxyflurane anesthesia is less than 2 minutes in all cases. The mortality rate with this hemorrhage protocol is approximately 12%, with all deaths occurring over the 24 hours post hemorrhage, and most deaths occurring within the one hour post hemorrhage.

With this hemorrhage model, anesthesia and cardiac puncture without blood withdrawal produced no changes in mitogen-induced lymphocyte proliferation, IL-2 receptor expression, phenotypic characteristics (CD3, CD4, CD8, B220, u, Ly-I expression) of B or T lymphocytes, cytokine (IL-2, IL-3, 11-4, IL-5, IL-10, IFN-γ) release, cytokine (IL-1α, IL-1β, IL-2, IL-5, IL-6, IL-10, TNFα, TGF-β, IFN-γ) mRNA levels, or splenic, intestinal, or pulmonary B cell clonal precursor frequencies. No evidence of hemothorax, bleeding into the pericardial space, lung or cardiac contusion has been found in surviving mice with this method of hemorrhage. No endotoxin is found in plasma obtained following hemorrhage in this model.

Mice were treated with 100 mg/kg Lisofylline in 0.2 ml PBS and given initially i.v., by retroorbital injection, then i.p. every 8 hours for a total of 9 doses. In hemorrhaged mice, the Lisofylline in PBS was added to the shed blood, and then given retroorbitally with the blood during the resuscitation phase. In hemorrhaged Balb/C mice (n=3), sacrificed by exsanguination 5 minutes after receiving Lisofylline with the blood used for resuscitation, serum levels of Lisofylline were 44±6 µg/ml.

Three days following hemorrhage and resuscitation or the initiation of treatment with Lisofylline therapy in normal treated animals, mice were anesthetized with methoxyflurane and sacrificed by exsanguination through cardiac puncture into a heparinized (5 U) syringe. Normal mice, not subjected to hemorrhage/resuscitation or to treatment with Lisofylline, were included. Bronchoalveolar lavage (BAL) specimens, using 1.0 ml PBS injected and aspiraed three times into the trachea and lungs, were obtained. Cells contained in the BAL were collected by centrifugation of BAL specimens. The supernatants were collected following centrifugation and stored at −70° C. until used for ELISA determination of cytokines. As determined by cytology, there was less than 3% contamination of alveolar macrophages with lymphocytes, neutrophils, or other mononuclear cell populations when BAL specimens. are collected in normal Balb/C mice, but approximately 11±2% of isolated cells are neutrophils in mice subjected 3 days previously to 30% blood volume hemorrhage with resuscitation one hour later. The BAL supernatants were collected and used for ELISA.

Intraparenchymal pulmonary mononuclear cells were isolated by collagenase digestion and Percoll® gradient purification using techniques previously described. Briefly, after the mouse was killed by cervical dislocation or exsanguination, the chest was opened and the lung vascular bed was flushed by injecting 3–5 ml of chilled (4° C.) PBS into the right ventricle. The lungs were then excised, avoiding the paratracheal lymph nodes, and washed twice in RPMI 1640. The lungs were minced finely, and the tissue pieces placed in RPMI 1640 with 5% FCS, penicillin/streptomycin, 10 mM HEPES, 50 µM 2-ME, 20 mM L-glutamine, containing 20 U/ml collagenase and 1 µg/ml DNase. Following incubation for 60 minutes at 37° C., any remaining intact tissue was disrupted by passage through a 21 gauge needle. Tissue fragments and the majority of dead cells were removed by rapid filtration through a glass wool column, and cells collected by centrifugation. The cell pellet was suspended in 4 ml of 80% Percoll® (Pharmacia, Uppsala, Sweden) and 4 ml of 40% Percoll® was then layered on. After centrifugation at 600 g for 20 minutes at 15° C., the cells at the interface were collected, washed in RPMI 1640, and counted. Viability, as determined by trypan blue exclusion, was consistently greater than 98%.

Peripheral blood mononuclear cells were isolated from heparinized blood which had been diluted 2:1 with PBS, pH 7.3, and layered onto a gradient containing 4 ml Lympholyte M (Accurate Chemicals, San Diego, Calif.). After centrifugation at 600 g for 20 minutes at 15° C., the cells at the interface were collected, washed in RPMI 1640, and counted. Viability, as determined by trypan blue exclusion, was consistently greater than 98%. Plasma was collected following centrifugation of blood to which had been added $10^{-3}$M EDTA.

mRNA was isolated using oligo dT cellulose minicoluinms (Invitrogen San Diego, Calif.). cDNA was synthesized from the mRNA of 100,000 cells for all cell populations except alveolar macrophages (where 20,000 cells were used) using Moloney murine leukemia virus reverse transcriptase and random hexamer oligonucleotides according to the procedure of Kawasaki (*PCR Protocols: A Guide to Methods and Applications*, Innis et al., eds, pp. 21–27, Academic Press, New York, 1991).

After a 2 minute, 94° C. denaturation step, between 30 and 40 cycles of PCR were carried out (45 seconds, 94° C. denaturation; 45 seconds, between 60° C. and 65° C. depending on the primer: 60° C. for IL-1β, IL-6, IFN-γ, and TNFα; and 65° C. for IL-10 annealing; and 2 minute, 72° C. extension) on cDNA from 1000 cells (10,000 cells from peripheral blood mononuclear cell populations). All cDNA samples for each cytokine were mixed with aliquots of the same PCR master mix. Cytokine MIMICs® (Clontech, Palo Alto, Calif.) was used for IL-1β, IL-6, IFN-γ, and TNFα, as well as the housekeeping gene glyceraldehyde 3 phosphate dehydrogenase (G3PDH) as internal controls for standardization of PCR product. DNA was amplified simultaneously for all experimental groups for each organ, using the G3PDH or cytokine MIMIC primer, and the cytokine primer of interest. The primers were used at 0.4 $\mu$M each (Clontech, Palo Alto, Calif.) except for IL-10, where the primer was synthesized commercially (Operon, Berkeley, Calif.) from the sequence determined by Moore et al., *Science* 248:1230, 1990.

To detect amplified cDNA, the PCR product was analyzed by agarose gel electrophoresis. The number of PCR cycles were selected for each cytokine product from each cellular population so that most of the ethidium bromide stained amplified DNA products were between barely detectable and below saturation. The gel was imaged using a video integration system (UVP, San Bernadino, Calif.) and then the relative intensities of the cytokine and control bands analyzed using computer integration programs (UVP, San Bernadino, Calif.). Cytokine densitometry results were normalized to those for G3PDH (IL-10) or the appropriate cytokine MIMIC (IL-1β, IL-6, TNFα, IFN-γ).

TNFα and IFN-γ concentrations in BAL supernatants and plasma were determined with sandwich ELISA assays using the monoclonal antibody pairs (i.e., unbiotinylated or biotinylated) MP6-XT3 for TNFα and XMG1.2 for IFN-γ (Pharmingen San Diego, Calif.). Briefly, ELISA plates (Immulon 4, Dynatech Laboratories, Chantilly, Va.) were coated overnight with the unbiotinylated antibody (5 $\mu$g/ml) in 0.05M phosphate buffer, pH 8. After washing the plates with PBS, the wells were saturated with PBS containing 1% BSA for 30 minutes at 37° C. After further washing with PBS, 50 $\mu$l of the BAL supernatant, plasma sample, or recombinant murine cytokine standard (TNFα, obtained from Genzyme, Boston, Mass. or IFN-γ from Pharmingen, San Diego, Calif.), in dilutions from 10 pg/ml to 3000 pg/ml, were placed in duplicate into the wells of the ELISA plates, and the plates incubated for 2 hours at room temperature. After washing, the biotinylated second antibody (1 $\mu$g/ml) in 50 $\mu$l PBS, 1% BSA was added to each well. After a further 1 hour incubation at room temperature, the plates were washed and 50 $\mu$l strepavidin/peroxidase conjugate (1:3000) (Southern Biological, Birmingham, Ala.) was added to each well for a further one hour incubation. After washing, the bound antibody was revealed with TMB/peroxidase substrate (Kirkegaard and Perry, Gaithersburg, Md.). The reaction was stopped 20 minutes later by addition of 2M $H_2SO_4$ (Stop Solution, Kirkegaard and Perry, Gaithersburg, Md.) to each well and the OD measured at 450 nm in a photometer (Titertek Multiscan, Flow Laboratories). Concentrations of TNFα and IFN-γ were calculated by comparison to a recombinant standard curve.

At 3 days following hemorrhage and resuscitation or the initiation of Lisofylline treatment, mice were sacrificed and the pulmonary circulation flushed with chilled PBS injected into the right ventricle, as described above. The left lower lobe of the lungs was placed into formalin. Hematoxylln and eosin sections of the lungs were prepared, and examined in a blinded fashion by a pulmonary pathologist who was unaware of the group to which the individual animal belonged. Lungs from normal, unmanipulated Balb/C mice also were included as additional controls. The histopathologic findings were scored on a 0 to 3 scale (with 0 being normal and 3 being the most severe change) for the following variables: a) neutrophil infiltration into the pulmonary interstitium; b) intraaveolar hemorrhage; and c) interstitial edema.

Groups of 6 to 8 mice were used for each condition. For each experimental condition, the whole group of animals was prepared and then studied at the same time. Cells, mRNA, BAL supernatants, and plasma were obtained individually from each animal, and then were analyzed individually before calculating group data. Data are presented as mean ± standard error of the mean (SEM) for each experimental group. One-way analysis of variance and the Student Newman Keuls test were used for comparisons between normal, nominal treated, hemorrhage/treated and hemorrhage data groups. A P value of less than 0.05 was considered significant.

In histologic findings in normal, hemorrhaged, and treated mice, marked neutrophil infiltration, intraaveolar hemorrhage, and interstitial edema, as previously described, were present in the lungs of mice subjected to hemorrhage and resuscitation 3 days previously. In mice treated with Lisofylline starting one hour after hemorrhage and during resuscitation with the shed blood, the degree of interstitial edema and intraaveolar hemorrhage was minimal, and not significantly different from that found in normal, unhemorrhaged and unmanipulated mice. The number of neutrophils in the pulmonary interstitium in hemorrhaged mice treated with Lisofylline was significantly decreased as compared to that found in hemorrhaged/resuscitated, but untreated animals, but remained greater than that present in normal unhemorrhaged and untreated mice. The number of neutrophils in the lungs of normal mice which had been treated with Lisofylline were significantly increased compared to normal, untreated animals, but remained significantly less than the number found in hemorrhaged or hemorrhaged, treated mice.

Significantly increased mRNA levels, as compared to those in normal mice, were present for IL-1β, IL-6, TNFα, and IFN-γ among intraparenchymal pulmonary mononuclear cells obtained 3 days following hemorrhage and resuscitation. Treatment of hemorrhaged/resuscitated mice with Lisoflline significantly decreased levels of mRNA for these cytokines. In hemorrhaged/resuscitated mice treated with Lisofylline, the amounts of mRNA among intraparenchymal pulmonary mononuclear cells for IL-1β, IL-6, TNFα, and IFN-γ were similar to those in normal, unmanipulated mice or in normal mice treated with Lisofylline. Despite 40 cycles of PCR, minimal amounts of IL-10 were found among intraparenchymal pulmonary mononuclear cells in all groups of mice. Therefore, no comparisons between groups for expression of IL-10 was possible.

Levels of mRNA for IL-1β and TNFα among the BAL cellular population isolated from mice 3 days following hemorrhage and resuscitation were significantly increased compared to those in normal mice. In hemorrhaged/resuscitated mice treated with Lisofylline starting one hour after blood loss, the amounts of mRNA for IL-β and TNFα among cells isolated from BAL samples were not different from those present among similarly isolated cells from normal, untreated or normal, Lisofylline treated mice. The percentage of neutrophils among BAL samples from hemorrhage/resuscitated mice treated with Lisofylline decreased to 6±2% from 11±2% in untreated hemorrhage/resuscitated mice (p<0.05). Despite 40 cycles of PCR, which should be capable of detecting 1 molecule per cell of cytokine, no expression for IL-6 was found in the BAL cellular population obtained in treated or untreated normal or hemorrhaged mice.

Figure 5:
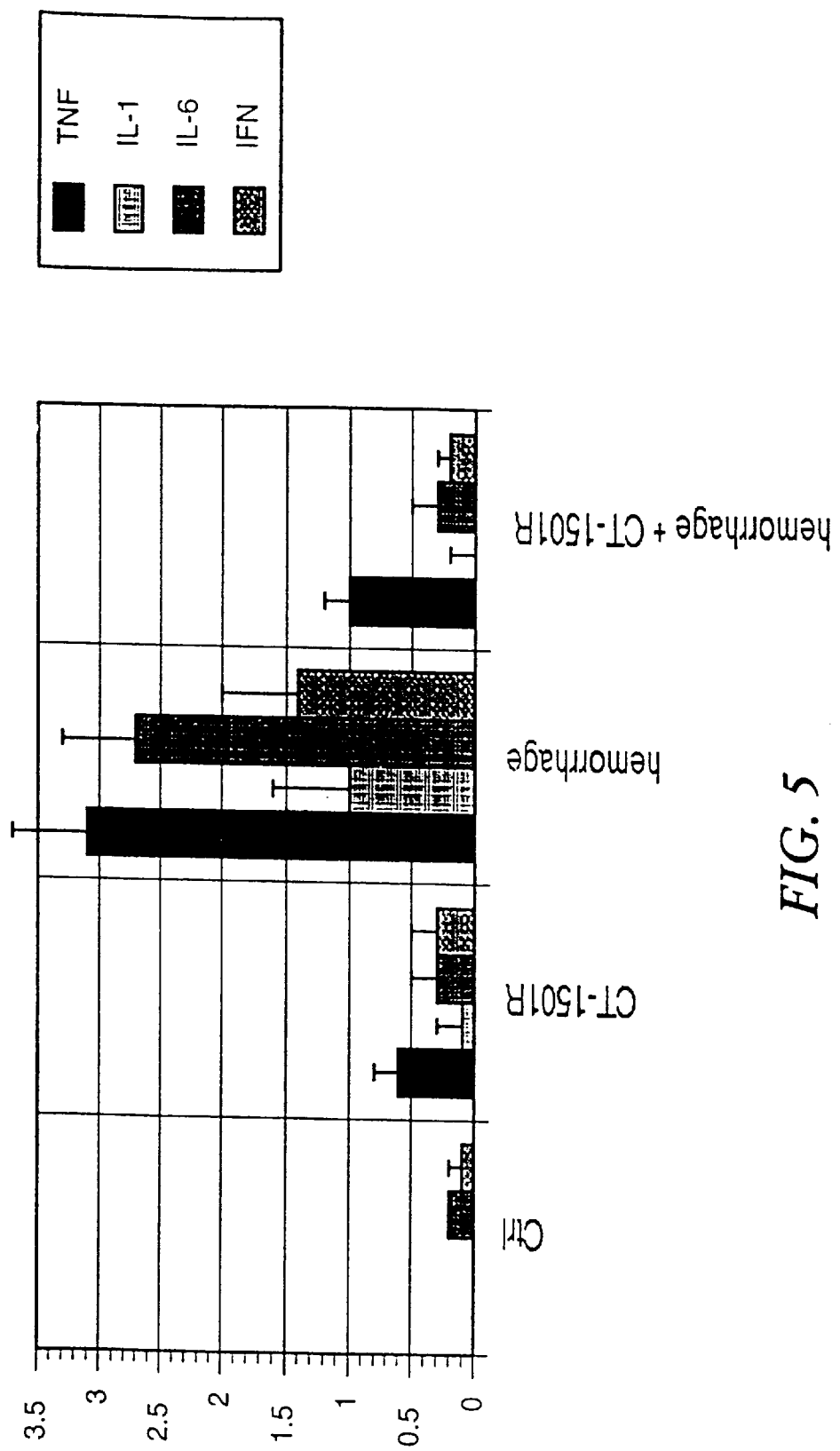
FIG. 5 shows the effect of CT1501R (1-R-(5-hydroxyhexyl)-3,7-dimethylxanthine or Lisofylline) on murine lung cytokine levels (determined by PCR) following hemorrhage and resuscitation. Lisofylline significantly decreased cytokine concentrations.
Figure 6:
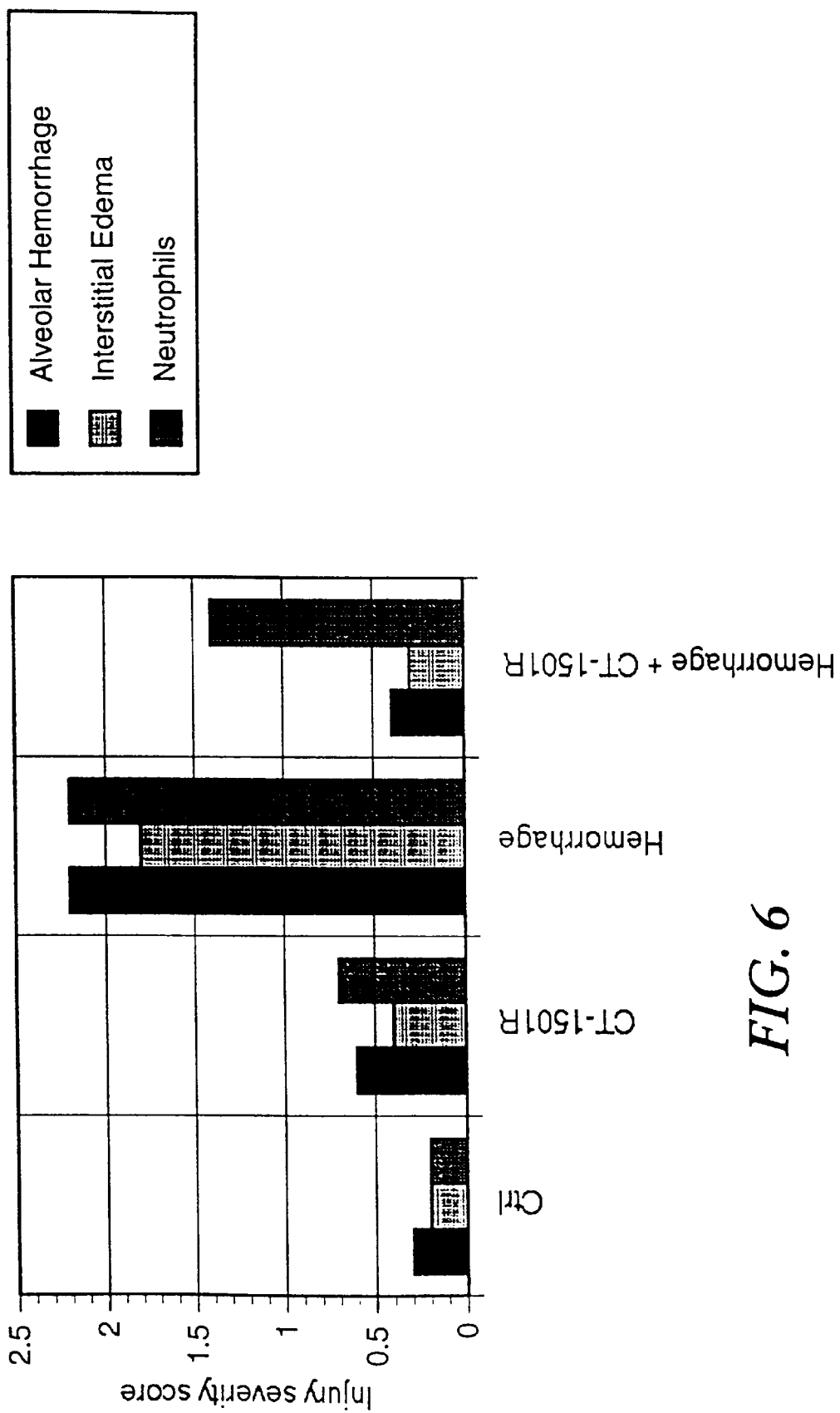
FIG. 6 shows the effect of Lisofylline on severity of lung injury in mice following hemorrhage shock. Alveolar hemorrhage, interstitial edema and neutrophils were measured.
Figure 7:
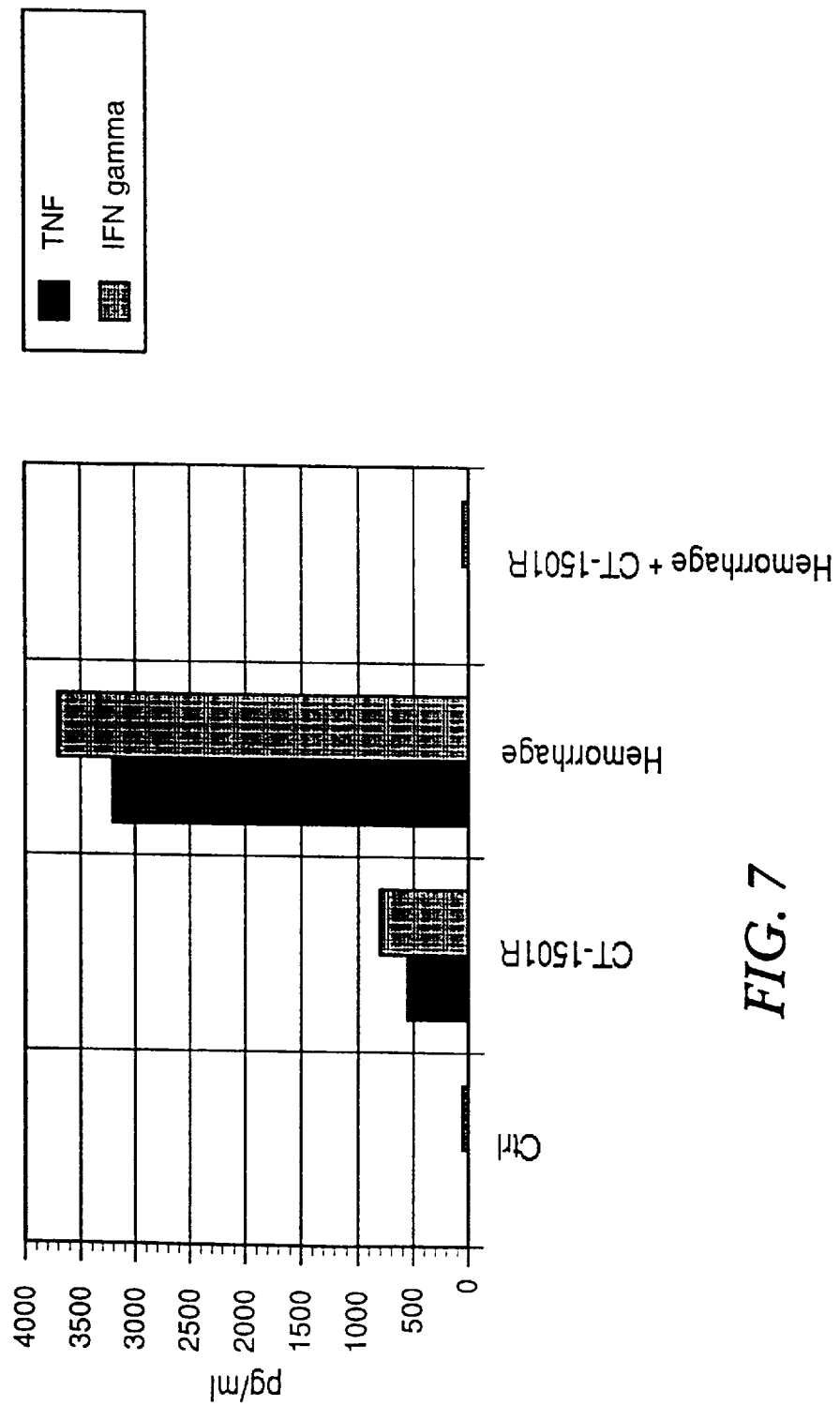
FIG. 7 shows the effect of Lisofylline on lung cytokine concentrations following hemorrhage shock in mice. Lisofylline significantly decreased cytokine levels in this model of ARDS.

PBMC obtained 3 days following hemorrhage and resuscitation had increased amounts of mRNA for TNFα, but not for IL-1β, IL-6, TNFα, and IFN-γ compared to that found in PBMC from normal, unmanipulated mice. In contrast, TNFα mRNA levels in PBMC from hemorrhage/resuscitated mice treated with Lisofylline were significantly decreased compared to levels in untreated mice subjected to hemorrhage and resuscitation 3 days previously. In these Lisofylline treated mice amounts of TNFα mRNA were not significantly different from those in normal mice or in nominal mice treated with Lisofylline. Treatment with Lisofylline after hemorrhage did not affect mRNA levels in PBMC for IL-1β, IL-6, TNFα, and IFN-γ (see FIGS. 5–7).

In normal mice, no IFN-γ in BAL supernatants or plasma was detected. In contrast, BAL supernatants and plasma from mice subjected to hemorrhage and resuscitation 3 days previously contained 163±31 and 406±150 pg/ml IFN-γ, respectively (p<0.001 versus normal for BAL supernatant and p<0.05 versus normal for plasma). In hemorrhaged/resuscitated mice treated with Lisofylline starting one hour after blood loss and continuing for 72 hours, IFN-γ levels were 2±2 pg/ml in BAL supernatants and 173±120 pg/ml in plasma (p<0.001 versus hemorrhaged/resuscitated untreated for BAL supernatants and p<0.05 versus hemorrhaged/resuscitated untreated for plasma; p=NS versus normal for BAL supernatants and plasma). In normal, unhemorrhaged mice, treated with Lisofylline, the IFN-γ content of BAL supernatants was 16±16 pg/ml and in plasma was 66±48 pg/ml (p=NS versus normal, untreated in each case).

Small amounts of TNFα were found in BAL supernatants and plasma from normal, unmanipulated Balb/C mice (77±64 pg/ml in BAL supernatants and 95±37 pg/ml in plasma). In BAL supernatants obtained 3 days following hemorrhage and resuscitation, TNFα content was significantly increased to 3607±184 pg/ml (p<0.001 versus normal). TNFα in BAL supernatants also was significantly increased in unhemorrhaged mice treated with Lisofyliine, 676±80 pg/ml (p<0.01 versus normal untreated). However, in hemorrhaged/resuscitated mice treated with Lisofylline, TNFα concentrations in BAL supernatants were 73±45 pg/ml (p=NS versus normal and p<0.001 versus TNFα concentrations in BAL supernatants from hemorrhaged/resuscitated mice which had not been treated with Lisofylline). Unlike the situation in BAL supernatants, where TNFα levels were significantly increased following hemorrhage and where TNFα levels were affected by therapy with Lisofylline in both normal and hemorrhaged mice, no significant alterations in plasma TNFα concentrations were found in hemorrhaged/resuscitated, hemorrhage/resuscitated/Lisofylline treated, or normal/Lisofylline treated mice, 172±52 pg/ml, 218±49 pg/ml, and 116±36 pg/ml, respectively (p=NS for all group comparisons).

Immunohistochemical staining of lung samples from normal mice showed no staining for TNFα. In sections from mice subjected to hemorrhage and resuscitation 3 days previously, staining for TNFα was present, particularly in the perivascular areas. However, in hemorrhaged/resuscitated mice or normal mice treated with Lisofylline, no signal for TNFα was detected, and the sections did not appear to be different in terms of their staining characteristics when compared to those from normal, untreated and unmanipulated mice.

EXAMPLE 2

This example illustrates that a highly-fatal and relatively common complication of septic shock is the development of acute non-cardiogenic lung injury (the Adult Respiratory Distress Syndrome, ARDS). Interleukin-1 (IL-1), Interleukin-8 (IL-8) and neutrophils (PMN) are increased in lungs of patients with ARDS and thought to contribute to lung injury. To evaluate this possibility and potential interactions, an intact and isolated rat lung models of acute lung injury which depend on IL-1 or IL-8 and neutrophils was developed. Injury in both of these models resembles changes which occur in lungs of ARDS patients, notably increased cellularity characterized by neutrophils and lung injury involving perivascular cuffing and edema.

Human recombinant interleukin-1α (IL-1) was obtained from Hoffmann-LaRoche, Inc. (Nutley, N.J.), frozen in aliquots and thawed daily for use. Ketainie hydrochloride was obtained from Parke-Davis (Morris Plains, N.J.), xylazine from Haver (New York, N.J.), $^{125}$I labeled bovine serum albumin (BSA) from ICN Radiochemicals (Irvine, Calif.), and heparin sodium from Elkins-Sinn, Inc. (Cherry Hill, N.J.). All other reagents were purchased from Sigma Chemical Co. (St. Louis, Mo.). Neutrophils were purified from human blood by well described methods. Venous blood was anticoagulated with heparin and the cellular elements were separated from platelet-rich plasma by centrifugation. Cell pellets were resuspended in platelet-poor plasma and diluted 1:4 with 6% dextran (Pharmacia Fine Chemicals, Piscataway, N.J.) in saline. Red cells were separated from leukocytes by sedimentation. Leukocyte-rich supernatants were then aspirated, underlain with Ficoll-Hypaque (Pharmacia Fine Chemicals), and centrifuged at 275×g to separate neutrophils and monocytes. Sedimented neutrophils were resuspended in Hank's balanced salt solution (HBSS). These preparations contained 94 to 96% neutrophils and 4 to 6% monocytes. All values were compared by analysis of variance and corrected by post hoc Student t tests for differences between groups. A p value of <0.05 was considered significant.

Neutrophil adherence was measured using the nylon fiber technique. Briefly, 50 mg of scrubbed nylon fiber (3-XXX), 3.81 cm type 200 (Travenol Laboratories, Deerfield, Ill.) was packed into the distal 10 mm of the barrels of tuberculin syringes. Ficoll-Hypaque-purified human neutrophils ($1\times10^7$ cells) in plasma (total volume, 0.25 ml) with and without Lisofylline were then placed in the top of the nylon fiber column which was maintained at 37° C. After 90 sec, the plunger was inserted and the samples were eluted. Eluted neutrophils were counted by hemocytometer, and percentages of neutrophils adhering to the nylon fiber were calculated by the following formula:

Neutrophils applied=elutedx100%/Neutrophils applied

Each sample was run in triplicate. Unstimulated locomotion was measured using control neutrophils in Hank's Balanced Salt Solution (HBSS) in the top chamber and HBSS in the bottom chamber. Stimulated locomotion was measured using twice-washed neutrophils in HBSS in the top chamber with and without Lisofylline and zymosan-activated serum (ZAS) in the bottom chamber. Neutrophils were deposited by centrifugation on a premoistened 5-$\mu$m Millipore filter (Millipore Corp., Worchester, Mass.) in the Boyden chamber. The chamber was incubated for 3 hours at 37° C. in room air. Indices of unstimulated or stimulated locomotion were expressed as the number of neutrophils migrating through the filter in 5 random, high-power objective fields (HPF).

Release of superoxide anion by neutrophils was determined spectrophotometrically by measuring superoxide dismutase (SOD) inhibitable reduction of horse heart ferricytochrome C (Sigma Chemical Co., St. Louis, Mo.). Briefly, neutrophils ($2 \times 10^6$) were placed in tubes containing HBSS (sufficient quantity to 2.0 ml), pooled human serum (1%), and SOD (2.98 mg) with and without Lisofylline. These mixtures were divided in half, and one part was incubated at 37° C. and one part at 4° C. After incubation, reaction mixtures were kept at 4° C. and centrifuged at 800xg for 15 min. Absorbance for paired supernatants was measured at 550 nm using a spectrophotometer (Model 35; Beckman Instruments, Inc., Fullerton, Calif.), averaged, and expressed at nanomoles of SOD-inhibitable cytochrome C reduced/20 min. In some experiments, neutrophils were incubated with PMA.

After Sprague-Dawley adult male rats (350±50 g) were anesthetized with pentobarbital (60 mg/kg i.p.), a tracheotomy cannula was placed and secured with 2-O ligature. Lungs were ventilated with a tidal volume of 3 cc at a rate of 60/min. with a gas mixture containing 5% $CO_2$ 21% $O_2$ and 74% $N_2$. Following midline thoracotomy, a 4-O ligature was loosely placed around the root of the pulmonary outflow tract. Heparin (200 units) was injected into the right ventricle and allowed to recirculate. A rigid cannula was placed into the right ventricle, threaded into the pulmonary outflow tract, and secured with the ligature. The left ventricle was incised and a drainage cannula was inserted and secured with a 2-O ligature. Lungs and heart were excised, placed in an isolated lung chamber, and ventilated with 2.5 cm of positive end-expiratory pressure. Lungs were perfused free of blood using Earle's Balanced Salt Solution (Sigma) containing calcium chloride (0.265 g/L), magnesium sulfate (0.09767 g/L), potassium chloride (0.4 g/L), sodium chloride (6.8 g/L), sodium phosphate monobasic (0.122 g/L) and D-glucose (1 g/L) to which was added sodium bicarbonate (2.2 g/L) and Ficoll-70 (Sigma)(40 g/L), and the final pH adjusted to 7.40. Perfusate (30 cc) was passed through the lungs to remove residual blood. The system was closed and 30 cc of perfusate was continuously recirculated at a rate of 40 cc/kg body wt/min. Pulmonary artery pressures were continuously monitored with a transducer and weight increases were monitored with a force transducer. A 20 min equilibration period was followed by a 60 min experimental protocol. After each experiment, a bronchoalveolar lavage with 5 cc of saline was performed (recovery was approximately 60%–80%) and saved for determination of Ficoll concentration.

Human recombinant IL-1$\alpha$ (50 ng in 0.5 cc saline) was injected into the trachea before the 20 min equilibration period. Purified human neutrophils ($4 \times 10^7$), with and without Lisofylline, were added to the persate chamber after the equilibration period. The final circulating concentration of neutrophils was $4 \times 10^7$ PMN/30 cc, or approximately 1,300 PMN/mm$^3$.

Interleukin-1$\alpha$ (IL-1) and Lisofylline administration in Male Sprague-Dawley rats weighing 300–350 g (Sasco, Omaha, Nebr.) were fed a normal diet and acclimated to altitude (Denver, Colo.) for at least 14 days before study. Rats were anesthetized with ketamine (90 mg/kg) and zylazine (7 mg/kg) intraperitoneally and then supplemented as needed with ketamine and zylazine and kept on a warming blanket. The trachea was cannulated with an indwelling 15 gauge stub adaptor tube. After 5 ventilated breaths (Harvard Apparatus Co., Millis, Mass.), IL-1 (0.5 ml, 50 ng) in sterile, endotoxin-free saline, was rapidly instilled intratracheally with a syringe, followed by another 5 ventilated breaths. Sham treated rats received identical anesthesia and surgery but were injected only with sterile saline intratracheally. In certain experiments, 20 mg/kg Lisofylline was administered intravenously just before (t=O) instillation of IL-1.

Saline (3.0 ml$\times$2) was slowly injected intratracheally and then withdrawn. Recovered lavage fluid was quantitated and centrifuged for 5 min and the cell pellet resuspended in 1.0 ml of lavage. Total cells were counted in a hemocytometer and a cytospin preparation (Shandon Southern Products Ltd, Cheshire, England) Wright-stained and examined to determine the percentages of neutrophils.

Lisofylline decreased human neutrophil chemotaxis to zymosan activated serum (ZAS) in vitro as shown in Table 3 below.

TABLE 3

| | Neutrophil Chemotaxis in Boyden Chambers in vitro (PMN/5HPF) |
|---|---|
| Neutrophils | 10.6 ± 0.4 (4)$\pi\delta$ |
| Neutrophils + ZAS | 31.1 ± 1.6 (5) |
| Neutrophils + ZAS + Lisofylline (50 $\mu$M) | 11.1 (2)$\delta$ |
| Neutrophils + ZAS + Lisofylline (1 $\mu$M) | 15.0 (2)$\delta$ |

$\pi$Mean ± S.E. (number of determinations)
$\delta$Value significantly different (p < 0.05) from value obtained for neutrophils + PMA Lisofylline decreased human neutrophil adherence to nylon fiber in vitro as shown in Table 4 below.

TABLE 4

| | Neutrophil Adherence (%) |
|---|---|
| Neutrophils | 40.4 ± 2.80 (5)$\pi\delta$ |
| Neutrophils + PMA | 71.0 ± 1.14 (5)$\pi$ |
| Neutrophils + PMA + Lisofylline (700 $\mu$M) | 26.6 ± 6.03 (5)$\delta$ |
| Neutrophils + PMA + Lisofylline (70 $\mu$M) | 25.6 ± 2.78 (5)$\delta$ |
| Neutrophils + PMA + Lisofylline (7 $\mu$M) | 38.8 ± 1.38 (4)$\delta$ |
| Neutrophils + PMA + Lisofylline (0.7 $\mu$M) | 35.8 ± 4.52 (4)$\delta$ |

$\pi$Mean ± S.E. (number of determinations)
$\delta$Value significantly different (p < 0.05) from value obtained for neutrophils + ZAS Lisofylline did not decrease human neutrophil superoxide anion production in vitro as shown in Table 5 below.

TABLE 5

|  | Neutrophil Superoxide Production in vitro ($\mu$M cyto c reduced/30 min) |
|---|---|
| Neutrophils | 2.1 ± 0.5 (4)πδ |
| Neutrophils + PMA | 80.6 ± 5.7 (4) |
| Neutrophils + PMA + Lisofylline (700 $\mu$M) | 92.0 ± 1.1 (4) |
| Neutrophils + PMA + Lisofylline (70 $\mu$M) | 80.6 ± 5.2 (4) |
| Neutrophils + PMA + Lisofylline (7 $\mu$M) | 82.3 ± 5.2 (4) |
| Neutrophils + PMA + Lisofylline (0.7 $\mu$M) | 9.2 ± 7.8 (4) |

πMean ± S.E. (number of determinations)
δValue significantly different ($p < 0.05$) from value obtained for neutrophils + PMA Lisofylline decreased injury in human neutrophil perfused isolated rat lungs given IL-8 intratracheally as shown in Table 6 below.

TABLE 6

|  | Lung Weight Gain (g) |
|---|---|
| Neutrophils | 0.37 ± 0.09 (6)πδ |
| IL-8 | 0.69 ± 0.15 (7)δ |
| Neutrophils + IL-8 | 3.03 ± 0.40 (8) |
| Neutrophils + IL-8 ± Lisofylline (50 $\mu$M) | 0.0 ± 0.0 (4)δ |
| Neutrophils + IL-8 ± Lisofylline (1 $\mu$M) | 0.0 ± 0.0 (3)δ |

πMean ± S.E. (number of determinations)
δValue significantly different ($p < 0.05$) from value obtained for neutrophils + IL-8

Lisofylline decreased neutrophils in lung lavages of intact rats given IL-1 intratracheally as shown in Table 7 below.

TABLE 7

| Treatment | Total Lavage PMNs (number × $10^6$) |
|---|---|
| Sham | 0.49 ± 0.21 (9)πδ |
| IL-1 | 5.10 ± 0.47 (8) |
| Sham + Lisofylline (100 $\mu$g/kg) | 0.42 ± 0.14 (8)δ |
| IL-1 + Lisofylline (100 $\mu$g/kg) | 3.64 ± 0.84 (9)δ |

πMean ± S.E. (number of determinations)
δValue significantly different ($p < 0.05$) from value obtained for IL-1

These data show that micromolar concentrations of Lisofylline decreased human neutrophil chemotaxis and adherence but not superoxide anion production in vitro. Treatment with Lisofylline also decreased IL-8 induced injury in isolated lungs perfused with neutrophils. Finally, treatment with Lisofylline decreased lavage neutrophil concentrations in lungs of intact rats given IL-1 intratracheally. Taken together, these data indicate that Lisofyiline can decrease neutrophil and cytokine mediated tissue injury and can treat or prevent a variety of diseases caused by tissue injury due to hypoxia

EXAMPLE 3

This example illustrates an experiment to show the effects of hypoxia on isolated human neutrophils. Briefly, 60 ml of heparinized blood was drawn from healthy human volunteers and overlayed with 2× volume of PBS onto LSM density 1.077 (Organon Teknika). The top layer including PMN and RBC's was mixed with 3% dextran (MW 298,000) and allowed to settle at room temperature for 30 min. The upper fraction, containing the PMN cells, was removed and the remaining RBC's lysed with cold 0.2% NaCl for 25 sec. An equal volume of 1.5% NaCl solution was added and the samples were centrifuged at 500×g for 5 min. The pellet was subjected to a second round of lysing RBC's, centrifuged and resuspended in RPMI-1640.

The PMN cells were subjected to hypoxia according to the conditions previously described in Rice et al., *Proc. Natl. Acad. Sci USA* 83:5978, 1986, whereby the cells were plated in Lux permanox plates, at $4 \times 10^6$ cells/ml and equilibrated with 95% $N_2$ and 5% $CO_2$ at 37° C. for 1.5 hr in nylon holders. Following the hypoxia, the cells were reaerated for various durations at 37° C. and fixed in 100% MeOH for lipid extraction and analysis by HPLC.

Figure 2:
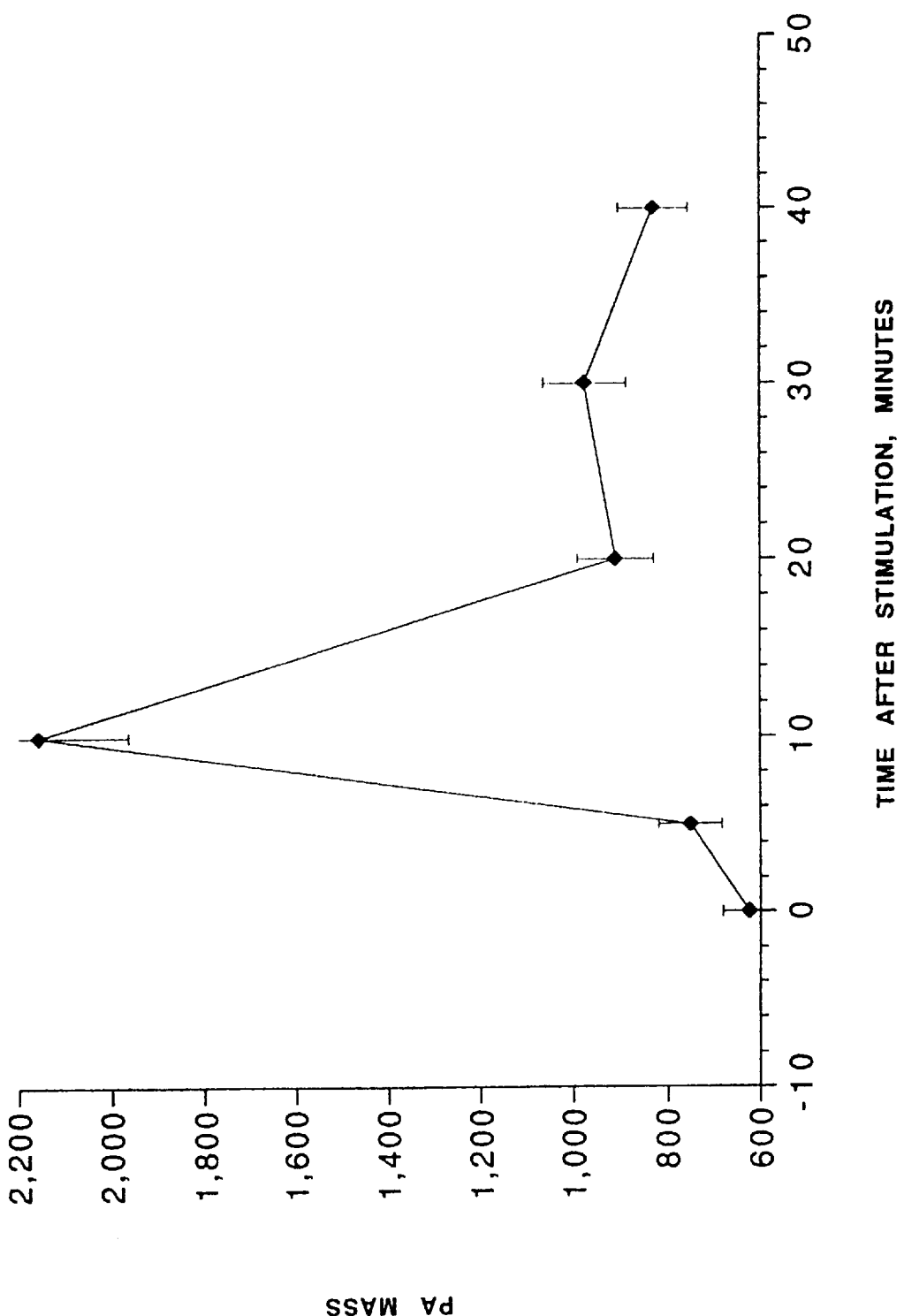
FIG. 2 shows the effect of hypoxia and reoxygenation in PMNs for PA. This PA species rises sharply and then falls.
Figure 3:
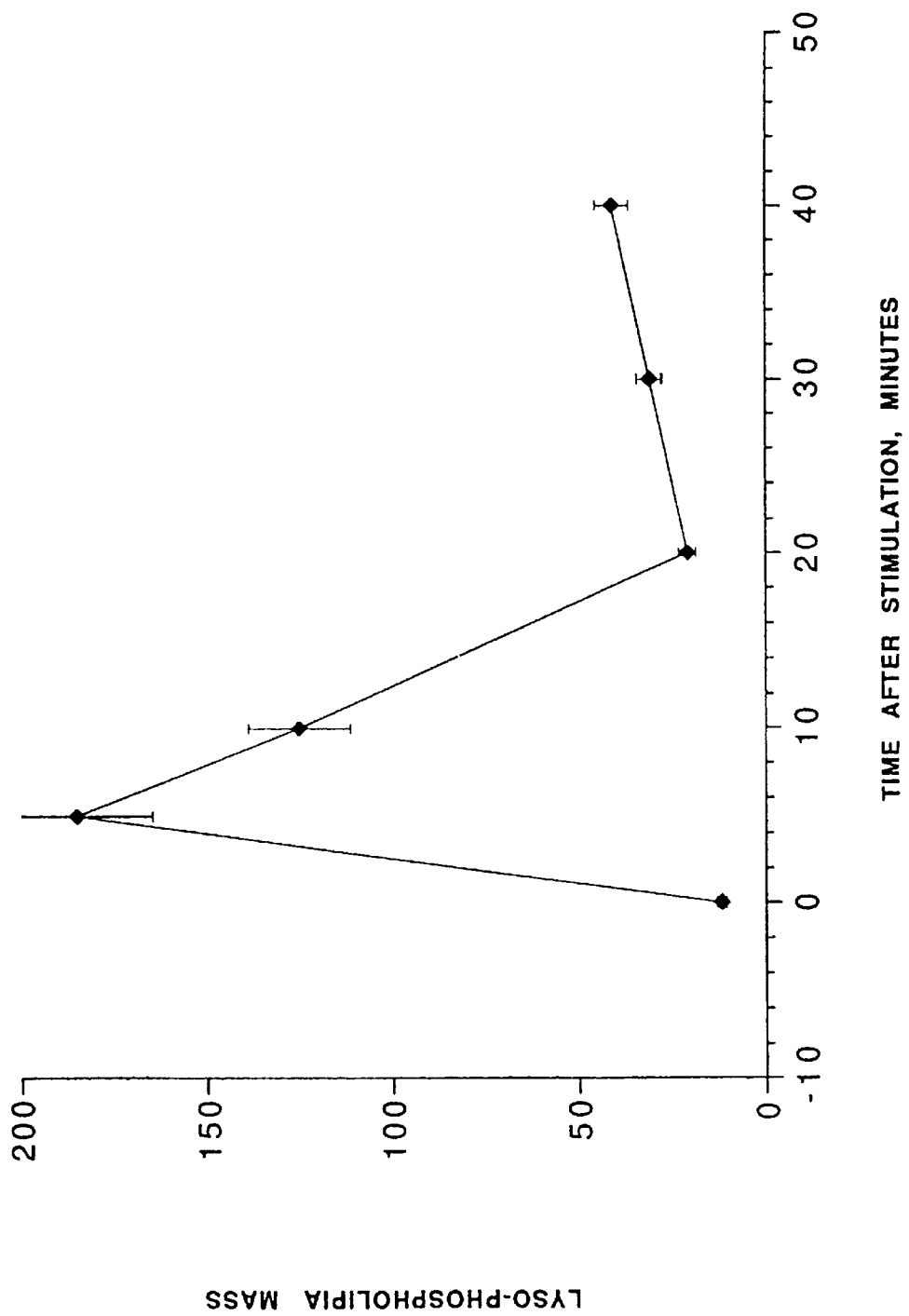
FIGS. 3 and 4 show the lipid mass of lysoPA fractions in PMNs with hypoxic stimulation followed by reoxygenation.
Figure 4:
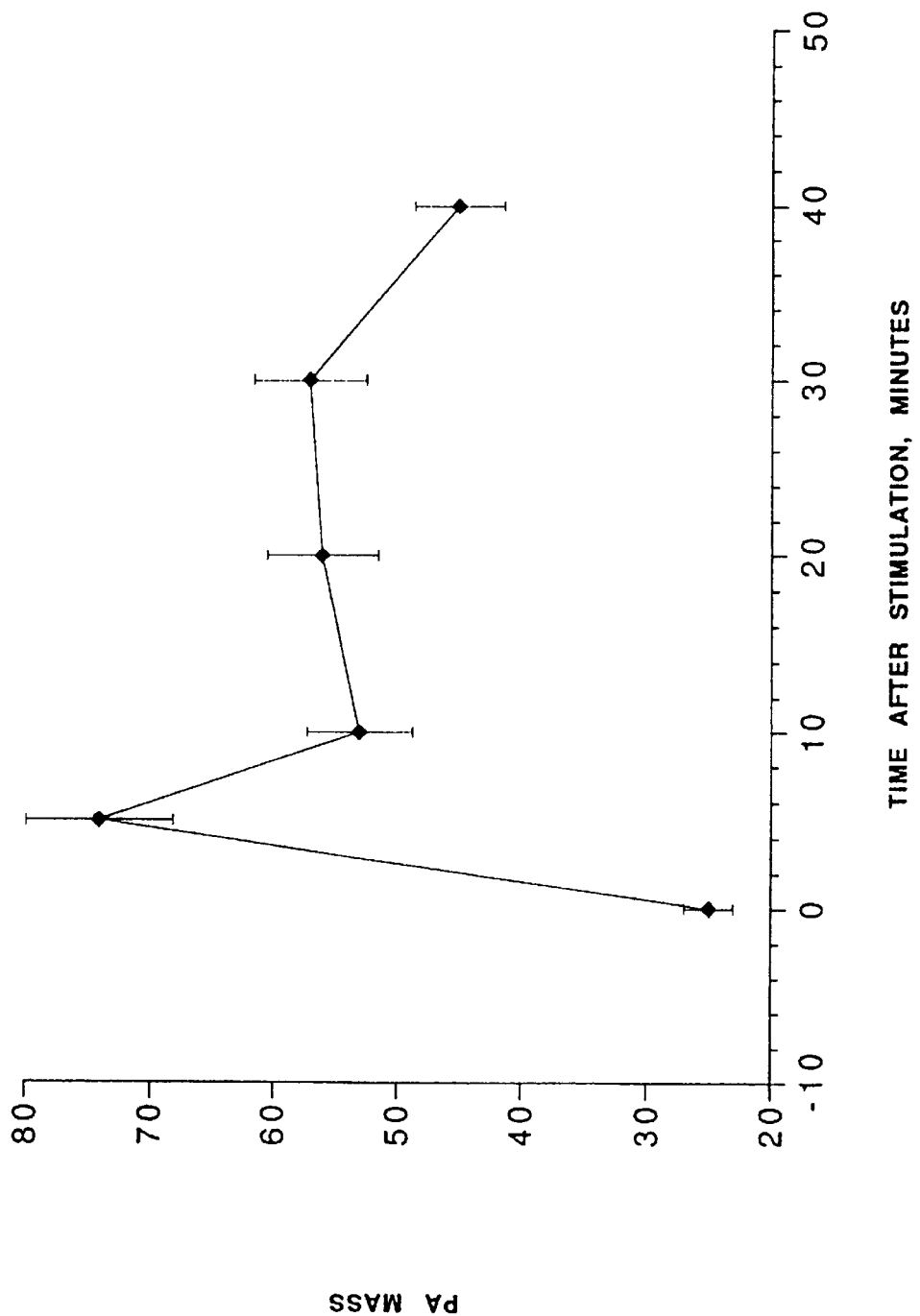

FIG. 1 shows the effect of hypoxia on non-arachidonyl PA concentrations in polymorphonuclear leukocytes (PMNs) by measuring PA mass after inducing hypoxia for 1 hour and reoxygenating for the times shown on the X axis. Cell PA concentrations rise over time in response to reoxygenation after hypoxia. FIG. 2 shows the effect of hypoxia and reoxygenation in PMNs for another PA species. This PA species rises sharply and then falls. FIGS. 3 and 4 show the lipid mass of lysoPA fractions in PMNs with hypoxic stimulation followed by reoxygenation. These data show that hypoxia followed by reoxygenation is a stimulus of the Pathway that leads to a proinflammatory cytokine cascade and is an in vitro model for hypoxia mediated diseases.

EXAMPLE 4

This example provides evidence from a group of experiments of the nexus and relationship between inhibiting linoleate-enriched PA species and reversal of hypoxic/reoxygenation tissue injury with Lisofylline. Lisofylline treated human neutrophils were exposed to hypoxia and then reoxygenation in vitro. Human neutrophils (PMN) were prepared from heparinized blood obtained from consenting, healthy human volunteers, isolated and highly purified (>99%) by percoll gradient and differential centrifugation and resuspended in HBSS (Hanks balanced salt solution). Human neutrophils were placed in hypoxia (95% $N_2$+5% $CO_2$) for 60 min and then reoxygenated (21% $O_2$+5% $CO_2$) for 20 min.

Following hypoxia/reoxygenation, human neutrophils had increased PA concentrations with a retention time (Rf) characteristic of linoleate-enriched PA species. The analysis was done by fixing the neutrophils in ice-cold methanol, extracting the lipids and then separating them by HPLC using a Waters $\mu$-Porosil silica column and an anisocratic gradient (Bursten et al., *J. Biol. Chem.* 266:20732, 1991). Lipids in the column effluent were monitored at 206–224 nm. HPLC fractions were also analyzed by thin layer chromatography (TLC), amine content, acyl content and mass spectroscopy to confirm peak identities. Fast-atom bombardment (FAB) mass spectroscopy spectra were acquired using a VG 70 SEQ tandem hybrid instrument of EBqQ geometry (VG Analytical, Altricham UK) as described in Bursten et al. The mass of total PA varied from 0.65–0.75% in unstimulated neutrophils to 2.7–3.6% of total detectable lipids in stimulated neutrophils (i.e., increased by 3.5–5 fold), whereas lyso-PA mass in neutrophils pretreated with Lisofylline and subject to hypoxia/reoxygenation stimulation could range as high as 7–8% of total detectable lipids. Hypoxia/reoxygenated neutrophils preincubated with 10 $\mu$M to 100 $\mu$M Lisofylline had decreased PA and increased lyso-PA total mass compared to untreated but stimulated neutrophils.

Neutrophil chemotactic activity was determined by Boyden chamber assay and quantitated as the number of migrating PMN/5HPF using zymosan-activated serum (ZAS) as the chemoattractant (Repine et al., *J. Reticuloendo. Soc.* 24:217, 1978). Neutrophil adherence was assessed by quantitating the percentage of neutrophils adhering to nylon fibers following addition of phorbol myristate acetate (PMA $10^{-6}$M, Sigma) (Rasp et al., *J. Reticuloendo. Soc.* 25:101, 1979). Neutrophil superoxide production was determined by quantitating superoxide dismutase inhibitable reduction of cytochrome c in response to PMA ($10^{-6}$M) (Berger et al., *J. Infectious Dis.* 149:413, 1984). Lisoflline treatment reduced stimulated human neutrophil adherence and chemotaxis but not neutrophil superoxide anion generation in vitro.

EXAMPLE 5

This example illustrates an in vivo kidney model of hypoxic tissue injury using Lisofylline. Isolated rat kidneys were rendered ischemic and reperfused with human neutrophils (prepared as in example 4 above) according to the procedure in Linas et al., *Am. J. Physiol.* 24:728–735, 1988. Lisofylline decreased injury in this ischemic isolated rat kidney model according to the data presented in Table 8 below wherein GFR refers to glomerular filtration rate and TNa refers to tubular sodium reabsorption.

TABLE 8

|  | Control | Ischemia + neutrophils | Ischemia + neutrophils + Lisofylline |
| --- | --- | --- | --- |
| GFR | 250 | 113 | 202 (n = 6) |
| TNa | 90% | 40% | 78% (n = 6) |

EXAMPLE 6

This example provides a discussion of the data presented in the foregoing examples. These data show that PA and linoleoyl PA in particular mediate multiple events responsible for the development of hypoxia/reoxygenation diseases using acute lung injury and ischemic kidneys as models. Lisofylline (a prototype compound that inhibits LPAAT and accumulation of linoleoyl PA in stimulated cells) treatment following blood loss decreased lung injury and lung neutrophil accumulation in mice subjected to hemorrhage-resuscitation, a finding paralleled by Lisofylline treatment decreasing neutrophil function in vitro. Systemic hypoxia followed by tissue reoxygenation, such as occurs in hemorrhage-resuscitation, induces the formation of linoleoyl PA in neutrophils as well as lung tissue. Increased production of PA then induces neutrophil chemotaxis, proinflammatory cytokine generation and lung injury.

Lisofylline also abrogated induction of mRNA for several proinflammatory cytokines in multiple cell types in the lungs of mice subjected to hemorrhage-resuscitation. These effects are explained by the basic signaling nature of linoleoyl PA on diverse components of the inflammatory cascade. Inflammatory stimuli translocate LPAAT to the plasma membrane (Bursten et al., *J. Biol. Chem.* 266:20732, 1991), therefore translocation and activation of LPAAT occur after oxidative stress. Adding PA to cells also produces potent mitogenic effects, stimulates calcium flux and phospholipase C activity, and induces expression of several protooncogenes and growth factors (Moolenaar et al., *Nature* 323:171, 1986; Altin et al., *Biochem J.* 247:613, 1987; and Knauss et al., *J. Biol. Chem.* 265:14457, 1990). Inhibition of LPAAT by Lisofylline appears to be the primary intracellular signaling pathway responsible for the observed effects on neutrophil function and lung injury. The IC50 of Lisofylline for inhibiting phosphodiesterase is between 100 and 500 $\mu$M in in vitro systems which is significantly higher than the concentrations (10–30 $\mu$M) at which Lisofylline effectively inhibits PA synthesis (Rice et al., *Proc. Natl. Acad. Sci. USA* 91:3857, 1994).

We claim:

1. A method for treating or preventing a disease caused by hypoxic tissue injury, comprising administering to a patient in need of such treatment a clinically achievable, effective amount of a compound that inhibits signal transduction by inhibiting cellular accumulation of linoleate-containing phosphatidic acid (PA) through an inhibition of the enzyme LPAAT (lysophosphatidic acyltransferase), wherein said compound has the formula:

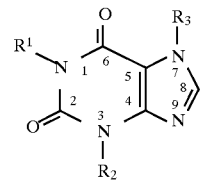

wherein $R_1$ is independently a resolved enantiomer of an $\omega$-1 secondary alcohol-substituted ($C_{5-12}$) alkyl, substantially free of the other enantiomer, and wherein each of $R_2$ and $R_3$ is independently a ($C_{1-12}$) alkyl, optionally containing one or two non-adjacent oxygen atoms in place of a carbon atom.

2. The method of claim 1 Wherein the disease that is a manifestation of hypoxia tissue injury is selected from the group consisting of: multiorgan dysfunction following shock caused by hemorrhage, severe cardiac dysfunction, severe burns, sepsis; CNS tissue injury following occlusive cerebrovascular accidents; stroke; cardiovascular tissue injury following myocardial infarction; organ dysfunction following transplantation of kidney, liver, heart, lung, or bowel; organ damage following vascular surgery in any site, peripheral angioplasty; high altitude pulmonary edema altitude sickness; acidosis; diabetic acidosis; drug acidosis; rendl acidosis; prevention of organ transplant rejection due to hypoxia; hypoxia-mediated neurodegenerative disease; Parkinsons diseases; Huntington's diseased; and ALS (Amyotrophic Lateral Sclerosis).

3. The method of claim 2 wherein the disease is ARDS.

4. A method for treating or preventing a disease caused by hypoxic tissue injury, comprising administering to a patient in need of such treatment a clinically achievable, effective amount of a compound that inhibits signal transduction by inhibiting cellular accumulation of linoleate-containing phosphatidic acid (PA) through inhibition of the enzyme LPAAT (lysophosphatidic acyltransferase), wherein said compound is a diastereomer, hydrate, salt, solvate or mixtures thereof, and has a straight or branched aliphatic hydrocarbon structure of formula I:

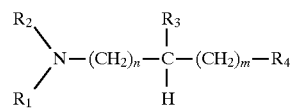

wherein n is an integer from one to four and m is an integer from four to twenty, $R_1$ and $R_2$ are independently hydrogen, a straight or branched chain alkyl, alkenyl or alkynyl of up to twenty carbon atoms in length or —$(CH_2)_w R_5$, wherein if $R_1$ or $R_2$ is —$(CH_2)_w R_5$, w is an integer from one to twenty and $R_5$ is a hydroxyl, halo, $C_{1-8}$ alkoxyl group or a substituted or unsubstituted carbocycle or heterocycle having from four to eight carbon atoms, N being a hetero atom of the resulting heterocycle, wherein $R_3$ is hydrogen, a hydroxy group, a $C_{1-3}$ straight or branched alkyl, or a $C_{1-3}$ alkoxy, wherein a total sum of carbon atoms comprising $R_1$ or $R_2$, $(CH_2)_n$ and $(CH_2)_m$ does not exceed forty, wherein $R_4$ is a terminal moiety comprising a substituted or unsubstituted heterocyclic moiety, wherein the heterocyclic moiety consists essentially of one to three ring structures having 5–7 members each, a hetero atom, and a predominantly planar structure or is essentially aromatic;

or the compounds include resolved enantiomers, diastereomers, hydrates, salts, solvates and mixtures thereof that have a straight or branched aliphatic hydrocarbon structure of formula II:

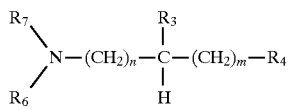

wherein n, m, $R_3$ and $R_4$ are defined as provided in formula I above, $R_6$ and $R_7$ are hydrogen, a straight or branched chain alkane, alkene or alkyne of up to twenty carbon atoms in length, or $-(CH_2)_x R_8$, wherein x is an integer from zero to fourteen and $R_8$ is a moiety having a general structure as provided in formula III:

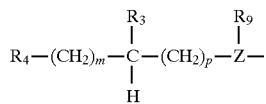

wherein m, $R_3$ and $R_4$ are defined as provided in formula I above, Z is N or CH and p is an integer from zero to four, wherein $R_9$ is H or a straight or branched chain alkane, alkene or alkyne of up to twenty carbon atoms in length.

5. The method of claim 4 wherein $R_4$ is selected from the group consisting of substituted or unsubstituted acridinyl; acridonyl; alkylpyridinyl; anthraquinonyl; ascorbyl; azaazulenyl; azabenzanthracenyl; azabenzanthrenyl; azabenzophenanthrenyl; azachrysenyl; azacyclazinyl; azaindolyl; azanaphthacenyl; azanaphthalenyl; azapyrenyl; azatriphenylenyl; azepinyl; azinoindolyl; azinopyrrolyl; benzacridinyl; benzazapinyl; benzofuryl; benzonaphthyridinyl; benzopyranonyl; benzopyranyl; benzopyronyl; benzoquinolinyl; benzoquinolizinyl; benzothiepinyl; benzothiophenyl; benzylisoquinolinyl; biotinyl; bipyridinyl; butenolidyl; butyrolactonyl; caprolactamyl; carbazolyl; carbolinyl; catechinyl; chromenopyronyl; chromonopyranyl; coumarinyl; coumaronyl; decahydroquinolinyl; decahydroquinolonyl; diazaanthracenyl; diazaphenanthrenyl; dibenzazepinyl; dibenzofuranyl; dibenzothiophenyl; dichromylenyl; dihydrofuranyl; dihydroisocoumarinyl; dihydroisoquinolinyl; dihydropyranyl; dihydropyridinyl; dihydropyridonyl; dihydropyronyl; dihydrothiopyranyl; diprylenyl; dioxanthylenyl; enantholactamyl; flavanyl; flavonyl; fluoranyl; fluorescienyl; furandionyl; furanochromanyl; furanonyl; furanoquinolinyl; furanyl; furopyranyl; furopyronyl; heteroazulenyl; hexahydropyrazinoisoquinolinyl; hydrofuranyl; hydrofurnanonyl; hydroindolyl; hydropyranyl; hydropyridinyl; hydropyrrolyl; hydroquinolinyl; hydrothiochromenyl; hydrothiophenyl; indolizidinyl; indolizinyl; indolonyl; isatinyl; isatogenyl; isobenzofurandionyl; isobenzofuranyl; isochromanyl; isoflavonyl; isoindolinyl; isoindolobenzazepinyl; isoindolyl; isoquinolinyl; isoquinuclidinyl; lactamyl; lactonyl; maleimidyl; monoazabenzonaphthenyl; naphthalenyl; naphthiindazopyridinedionyl; naphthindolizinedionyl; naphthodihydropyranyl; naphthofuranyl; naphthothiophenyl; naphthyridinyl; oxepinyl; oxindolyl; oxolenyl; perhydroazolopyridinyl; perhydroindolyl; phenanthraquinonyl; phenanthridinyl; phenanthrolinyl; phthalideisoquinolinyl; phthalirnidyl; phthalonyl; piperidinyl; piperidonyl; prolinyl; pyradinyl; pyranoazinyl; pyranoazolyl; pyranopyrandionyl; pyranopyridinyl; pyranoquinolinyl; pyranopyradinyl; pyranyl; pyrazolopyridinyl; pyridinethionyl; pyridinonaphthalenyl; pyridinopyridinyl; pyridinyl; pyridocolinyl; pyridoindolyl; pyridopyridinyl; pyridopyrimidinyl; pyridopyrrolyl; pyridoquinolinyl; pyronyl; pyrrocolinyl; pyrrolidinyl; pyrrolizidinyl; pyrrolizinyl; pyrrolodiazinyl; pyrrolonyl; pyrrolopyrimidinyl; pyrroloquinolonyl; pyrrolyl; quinacridonyl; quinolinyl; quinolizidinyl; quinolizinyl; quinolonyl; quinuclidinyl; rhodaminyl; spirocoumaranyl; succinimidyl; sulfolanyl; sulfolenyl; tetrahydrofranyl; tetrahydroisoquinolinyl; tetrahydropyranyl; tetrahydropyridinyl; tetrahydrothiapyranyl; tetrahydrothiophenyl; tetrahydrothiopyranonyl; tetrahydrothiopyranyl; tetronyl; thiabenzenyl; thiachromanyl; thiadecalinyl; thianaphthenyl; thiapyranyl; thiapyronyl; thiazolopyridinyl; thienopryidinyl; thienopyrrolyl; thienothiophenyl; thiepinyl; thiochromenyl; thiocoumarinyl; thiophenyl; thiopyranyl; triazaanthracenyl; triazinoindolyl; triazolopyridinyl; tropanyl; xanthenyl; xanthonyl, xanthydrolyl, adeninyl; alloxanyl; alloxazinyl; anthranilyl; azabenzanthrenyl; azabenzonaphthenyl; azanaphthacenyl; azaphenoxazinyl; azapurinyl; azinyl; azoloazinyl; azolyl; barbituric acid; benzazinyl; benziridazolethionyl; benzimidazolonyl; benzimidazolyl; benzisothiazolyl; benzisoxazolyl; benzocinnolinyl; benzodiazocinyl; benzodioxanyl; benzodioxolanyl; benzodioxolyl; benzopyridazinyl; benzothiazepinyl; benzothiazinyl; benzothiazolyl; benzoxazinyl; benzoxazolinonyl; benzoxazolyl; cinnolinyl; depsidinyl; diazaphenanthrenyl; diazepinyl; diazinyl; dibenzoxazepinyl; dihydrobenzimidazolyl; dihydrobenzothiazinyl; dihydrooxazolyl; dihydropyridazinyl; dihydropyrimidinyl; dihydrothiazinyl; dioxanyl; dioxenyl; dioxepinyl; dioxinonyl; dioxolanyl; dioxolonyl; dioxopiperazinyl; dipyrimidopyrazinyl; dithiolanyl; dithiolenyl; dithiolyl; flavinyl; furopyrimidinyl; glycocyamidinyl; guaninyl; hexahydropyrazinoisoquinolinyl; hexahydropyridazinyl; hydantoinyl; hydroimidazolyl; hydropyrazinyl; hydropyrazolyl; hydropyridazinyl; hydropyrirnidinyl; imnidazolinyl; irnidazolyl; imidazoquinazolinyl; imidazothiazolyl; indazolebenzopyrazolyl; indoxazenyl; inosinyl; isoalioxazinyl; isothiazolyl; isoxazolidinyl; isoxazolinonyl; isoxazolinyl; isoxazolonyl; isoxazolyl; lumazinyl; methylthyminyl; methyluracilyl; morpholinyl; naphthimidazolyl; oroticyl; oxathianyl; oxathiolanyl; oxazinonyl; oxazolidinonyl; oxazolidinyl; oxazolidonyl; oxazolinonyl; oxazolinyl; oxazolonyl; oxazolopyrimidinyl; oxazolyl; perhydrocinnolinyl; perhydropyrroloazinyl; perhydropyrrolooxazinyl; perhydropyrrolothiazinyl; perhydrothiazinonyl; perimidinyl; phenazinyl; phenothiazinyl; phenoxathiinyl; phenoxazinyl; phenoxazonyl; phthalazinyl; piperazindionyl; piperazinodionyl; polyquinoxalinyl; pteridinyl; pterinyl; purinyl; pyrazinyl; pyrazolidinyl; pyrazolidonyl; pyrazolinonyl; pyrazolinyl; pyrazolobenzodiazepinyl; pyrazolonyl; pyrazolopyridinyl; pyrazolopyrimidinyl; pyrazolotriazinyl; pyrazolyl; pyridazinyl; pyridazonyl; pyndopyrazinyl; pyndopymidinyl; pyrimidinethionyl; pyrimidinyl; pyrimidionyl; pyrimidoazepinyl; pynmidopteridinyl; pyrrolobenzodiazepinyl; pyrrolodiazinyl; pyrrolopyrimidinyl; quinazolidinyl;

quinazolinonyl; quinazolinyl; quinoxalinyl; sultamyl; sultinyl; sultonyl; tetrahydrooxazolyl; tetrahydropyrazinyl; tetrahydropyridazinyl; tetrahydroimoxinyl; tetrahydrothiazolyl; thiazepinyl; thiazinyl; thiazolidinonyl; thiazolidinyl; thiazolinonyl; thiazolinyl; thiazolobenzimidazolyl; thiazolyl; thienopyrimidinyl; thiazolidinonyl; thyminyl; triazolopyrimidinyl; uracilyl; xanthinyl; xylitolyl; azabenzonaphthenyl; benzofuroxanyl; benzothiadiazinyl; benzotriazepinonyl; benzotriazolyl; benzoxadizinyl; dioxadiazinyl; dithiadazolyl; dithiazolyl; fazanyl; furoxanyl; hydrotriazolyl; hydroxytrizinyl; oxadiazinyl; oxadiazolyl; oxathiazinonyl; oxatriazolyl; pentazinyl; pentazolyl; petrazinyl; polyoxadiazolyl; sydononyl; tetraoxanyl; tetrazepinyl; tetrazinyl; tetrazolyl; thiadiazinyl; thiadiazolinyl; thiadiazolyl; thiadioxazinyl; thiatriazinyl; thiatriazolyl; thiatriazolyl; triazepinyl; triazinoindolyl; triazinyl; triazolinedionyl; triazolinyl; triazolyl; trioxanyl; triphenodioxazinyl; triphenodithiazinyl; trithiadiazepinyl; trithianyl; trixolanyl.

6. A method for treating cystic fibrosis, comprising administering to a patient in need of such treatment an effective amount of a compound that inhibits signal transduction by inhibiting cellular accumulation of non-arachidonyl, linoleate- or myristylate-containing PA, through inhibition of the enzyme LPAAT, wherein said compound has the formula:

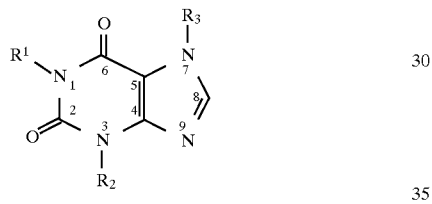

wherein $R_1$ is independently a resolved enantiomer of an ω-1 secondary alcohol-substituted ($C_{5-12}$) alkyl, substantially free of the other enantiomer, and wherein each of $R_2$ and $R_3$ is independently a ($C_{1-12}$) alkyl, optionally containing one or two non-adjacent oxygen atoms in place of a carbon atom.

7. A method for treating cystic fibrosis, comprising administering to a patient in need of such treatment an effective amount of a compound that inhibits signal transduction by inhibiting cellular accumulation of non-arachidonyl, linoleate- or myristylate-containing PA through an inhibition of the enzyme LPAAT, wherein said compound is a diastereomer, hydrate, salt, solvate or mixtures thereof, and has a straight or branched aliphatic hydrocarbon structure of formula I:

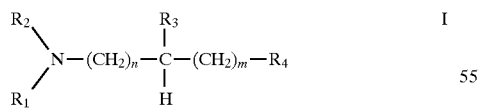

wherein n is an integer from one to four and m is an integer from four to twenty, $R_1$ and $R_2$ are independently hydrogen, a straight or branched chain alkyl, alkenyl or alkynyl of up to twenty carbon atoms in length or $-(CH_2)_wR_5$, wherein if $R_1$ or $R_2$ is $-(CH_2)_wR_5$, w is an integer from one to twenty and $R_5$ is a hydroxyl, halo, $C_{1-8}$ alkoxyl group or a substituted or unsubstituted carbocycle or heterocycle having from four to eight carbon atoms, N being a hetero atom of the resulting heterocycle, wherein $R_3$ is hydrogen, a hydroxy group, a $C_{1-3}$ straight or branched alkyl, or a $C_{1-3}$ alkoxy, wherein a total sum of carbon atoms comprising $R_1$ or $R_2$, $(CH_2)_n$ and $(CH_2)_m$ does not exceed forty, wherein $R_4$ is a terminal moiety comprising a substituted or unsubstituted heterocyclic moiety, wherein the heterocyclic moiety consists essentially of one to three ring structures having 5–7 members each, a hetero atom, and a predominantly planar structure or is essentially aromatic;

or the compounds include resolved enantiomers, diastereomers, hydrates, salts, solvates and mixtures thereof that have a straight or branched aliphatic hydrocarbon structure of formula II:

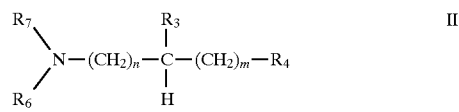

wherein n, m, $R_3$ and $R_4$ are defined as provided in formula I above, $R_6$ and $R_7$ are hydrogen, a straight or branched chain alkane, alkene or alkyne of up to twenty carbon atoms in length, or $-(CH_2)_xR_8$, wherein x is an integer from zero to fourteen and $R_8$ is a moiety having a general structure as provided in formula III:

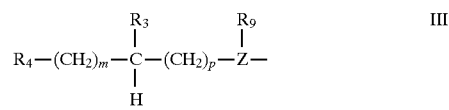

wherein m, $R_3$ and $R_4$ are defined as provided in formula I above, Z is N or CH and p is an integer from zero to four, wherein $R_9$ is H or a straight or branched chain alkane, alkene or alkyne of up to twenty carbon atoms in length.

* * * * *